(12) United States Patent
Albert et al.

(10) Patent No.: US 9,982,007 B2
(45) Date of Patent: *May 29, 2018

(54) COCRYSTALS OF PROGESTERONE

(71) Applicant: AMRI SSCI, LLC, West Lafayette, IN (US)

(72) Inventors: Ekaterina Albert, West Lafayette, IN (US); Patricia Andres, West Lafayette, IN (US); Melanie Janelle Bevill, West Lafayette, IN (US); Jared Smit, Lafayette, IN (US); Jennifer Nelson, Kokomo, IN (US)

(73) Assignee: AMRI SSCI, LLC, West Lafayette, IN (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/333,691

(22) Filed: Oct. 25, 2016

(65) Prior Publication Data

US 2017/0101433 A1 Apr. 13, 2017

Related U.S. Application Data

(63) Continuation of application No. 14/017,397, filed on Sep. 4, 2013, now Pat. No. 9,512,166.

(60) Provisional application No. 61/696,899, filed on Sep. 5, 2012.

(51) Int. Cl.
*C07J 7/00* (2006.01)

(52) U.S. Cl.
CPC .......... *C07J 7/002* (2013.01); *C07B 2200/13* (2013.01)

(58) Field of Classification Search
CPC .............................. C07J 7/002; C07B 2200/13
USPC ......................................................... 552/607
See application file for complete search history.

(56) References Cited

U.S. PATENT DOCUMENTS

| | | |
|---|---|---|
| 7,452,555 B2 | 11/2008 | Childs |
| 8,212,079 B2 | 7/2012 | Childs |
| 8,350,085 B2 | 1/2013 | Childs |
| 9,120,766 B2 | 9/2015 | Bevill et al. |
| 2011/0251426 A1 | 10/2011 | Childs et al. |
| 2014/0073674 A1 | 3/2014 | Bevill et al. |
| 2015/0216851 A1 | 8/2015 | Bevill et al. |

OTHER PUBLICATIONS

Ekaterina Bakhmutova-Albert et al, Enhancing Aqueous Dissolution Rates of Progesterone via Cocrystallization, Poster, AAPS Meeting (Oct. 14-17, 2012).

Ekaterina Bakhmutova-Albert et al, Enhancing Aqueous Dissolution Rates of Progesterone via Cocrystallization, Absract, AAPS (Oct. 14-17, 2012).
Etter, Margaret C. et al., "Graph-Set Analysis of Hydrogen-Bond Patterns in Organic Crystals," Acta Cryst., B46, pp. 256-262 (1990).
Etter, Margaret C. et al., "The Use of Cocrystallization as a Method of studying Hydrogen Bond Preferences of 2-Aminopyridine," Journal of the Chemical Society, Chemical Communications, No. 8, pp. 589-591 (1990).
Flack, HD., "On Enantiomorph-Polarity Estimation," Acta Cryst., A39, pp. 876-881 (1983).
Gorbitz, C.H. et al., "On the inclusion of solvent molecules in the crystal structures of organic compounds," Acta Cryst., B56, pp. 526-534(2000).
Hooft, R.W.W. et al., "Determination of absolute structure using Bayesian statistics on Bijvoet differences", J. Appl. Cryst., vol. 41, pp. 96-103 (2008).
Kumar et al., "Molecular Complexes of Some Mono- and Dicarboxylic Acids with trans-1 ,4-Dithiane-1 ,4-dioxide," American Chemical Society, Crystal Growth & Design, vol. 2, No. 4, pp. 313-318 (2002).
Schultheiss, N. et al., "Nutraceutical cocrystals: utilizing pterostilbene as a cocrystal former," Crystal Engineering Communications, vol. 12, pp. 2436-2442 (2010).
Schultheiss, N. et al., "Attempted construction of minoxidil: carboxylic acid cocrystals; 7 salts and 1 cocrystal resulted," Crystal Engineering Communications, vol. 12, pp. 742-749 (2010).
Schultheiss. N. et al.. "Attempted construction of minoxidil: carboxylic acid cocrystals; 8 salts and 1 cocrystal resulted," Crystal Engineering Communications, Supplementary Material, pp. 1-19 (2010).
Schultheiss, N. et al., "Nifedipine--pyrazine (2/1)," Acta Cryst. E66, pp. 2297-2298 and Sup-1 to Sup-9 (2010).
Ivanisevic et al., "Use of X-Ray Powder Diffraction in the Pharmaceutical Industry," Pharm. Sci. Encycl. pp. 1-42 (2010).
Bhattacharya et al. "Thermoanalyical and Crystallographic Methods" in Brittain H. ed. 2nd ed. Informa Healthcare:NY, pp. 318-335(2009).
Aakeroy, "Crystal Engineering: Strategies and Architectures ," Acta Cryst. B53, pp. 569-586 (1997).
Sekhon BS, "Pharmaceutical co-crystals—a review," Ars Pharm. 50(3): 99-117 (2009).
Kirk-Othmer Encyclopedia of Chemical Technology, 8, pp. 95-147 (2002).

(Continued)

*Primary Examiner* — Barbara P Badio
(74) *Attorney, Agent, or Firm* — LeClairRyan PLLC

(57) ABSTRACT

The present invention relates to a cocrystal of progesterone and a coformer selected from the group consisting of vanillic acid, benzoic acid, salicylic acid, cinnamic acid, and vanillin. The present invention also relates to a pharmaceutical composition comprising a cocrystal of the present invention and at least one pharmaceutically acceptable carrier. The present invention further relates to a method of supplementing progesterone in women. This method involves administering to a female subject in need thereof a pharmaceutical composition of the present invention.

20 Claims, 31 Drawing Sheets

(56) References Cited

OTHER PUBLICATIONS

Haleblian et al., "Pharmaceutical Applications of Polymorphism," Journal of Pharmaceutical Sciences 58(8), pp. 911-929 (1969).
Bernstein, "Polymorphism in Molecular Crystals," pp. 115-118 and 272 (2002).
United States Patent and Trademark Office, Non-Final Office Action for U.S. Appl. No. 13/657,259, dated Jul. 24, 2014.
Wolfe et al., "Polymorphic Cocystals" Poster, AAPS Meeting (2010).
Bevill et al., "Phase Diagrams Illustrating Solubility and Gibb's Free Energy of 1:1 and 2:1 Cocrystals of Nutraceutical p-Coumaric Acid with Nicotinamide," Abstract ID: AM-12-02982 (Jun. 8, 2012).
Bevill et al., "Polymorphic Cocrystals of Nutraceutical Compound p-Coumaric Acid with Nicotinamide: Characterization, Relative Solid-State Stability, and Conversion to Alternate Stoichiometries," Cryst. Grow1h Des., pp. 1438-1448 (2014).
Bevill et al., "Phase Diagrams Illustrating Solubility and Gibb's Free Energy of 1:1 and 2:1 Cocrystals of Nutraceutical p-Coumaric Acid with Nicotinamide," Poster, AAPS Meeting (2012).
David C. Lee and Michael L. Webb, Pharmaceutical Analysis, 2003, pp. 254-259, 1st edition, CRC Press, Boca Raton, Florida, United States of America.
Nate Schultheiss, et ai, Cocrystals of nutraceutical p-coumaric acid with caffeine and theophylline: polymorphism and solid-state stability explored in detail using their crystal graphs, CrystEngComm, Sep. 22, 2010, pp. 611-619,13, The Royal Society of Chemistry, London, United Kingdom.
United States Patent and Trademark Office, Non-Final Office Action for U.S. Appl. No. 13/657,259, dated Jul. 24, 2014, Alexandra, Virginia.

ORTEP Drawing of Cocrystal 1

ORTEP Drawing of Cocrystal 2

ORTEP Drawing of Cocrystal 4

ORTEP Drawing of Cocrystal 5

COCRYSTALS OF PROGESTERONE

This is a continuation application of U.S. patent application Ser. No. 14/017,397, filed Sep. 4, 2013, which claims priority to U.S. Provisional Patent Application Ser. No. 61/696,899, filed on Sep. 5, 2012, which are incorporated herein by reference in their entirety.

BACKGROUND

Progesterone is a naturally occurring steroid which is secreted from ovaries, placenta, and the adrenal gland and supports gestation. Progesterone is also available as a medication and is used for progesterone supplementation or replacement treatment for infertile women with progesterone deficiency. It is also indicated for the treatment of secondary amenorrhea. In the United States, pharmaceutical compositions of progesterone are available as vaginal gels, vaginal inserts, injections, or oral capsules. Progesterone is poorly soluble in water and bioavailability is low when taken orally.

The structure of progesterone is shown in FIG. 31.

Progesterone is known to exist in two polymorphic forms, I and II, with form II being a metastable form (*J. Pharm Sci.* 96:3419-31 (2007)). Cocrystals of progesterone have been disclosed in the literature. These include progesterone hydroquinone monohydrate (1:1:1) (*J. Crys. Spec. Research*, 19:983 (1989)); progesterone:indole (1:2) (Mar. 1, 2001 *Acta Crystallogr.*, Sect. A: Cryst. Phys., Diffr., Theor. Crystallogr. (1981), 37, C56); pregnolone:progesterone (*J. Pharm Sci.* 96:3419-31 (2007)); resorcinol:progesterone (*Acta Cryst.* B31:637 (1975)) as are others (see *PNAS* 103:13216-13221 (2010) and US2005018041).

A cocrystal of a compound is a distinct chemical composition between the compound and coformer, and generally possesses distinct crystallographic and spectroscopic properties when compared to those of the compound and coformer individually. A coformer is also a compound and is often referred to as a "guest." The compound which is not the coformer is often referred to as the "host." Unlike salts, which possess a neutral net charge, but which are comprised of charge-balanced components, cocrystals are comprised of neutral species. Thus, unlike a salt, one cannot determine the stoichiometry of a cocrystal based on charge balance. Indeed, one can often obtain cocrystals having molar ratios of compound to coformer of greater than or less than 1:1. The molar ratio of the components is a generally unpredictable feature of a cocrystal.

Cocrystals have the potential alter physicochemical properties. More specifically, cocrystals have been reported to alter aqueous solubility and/or dissolution rates, increase stability with respect to relative humidity, and improve bioavailability of active pharmaceutical ingredients with respect to other cocrystals of such ingredients. The coformer, or guest, is often varied or selected for purposes of altering such properties.

The chemical composition of a cocrystal, including the molar relationship between the coformer and the compound (such as an API) can be determined by single crystal x-ray analysis. Where such an analysis is not available, often solution-state proton NMR is used to verify composition and identify molar ratio.

Cocrystal formation may be further confirmed by comparing solid-state analytical data of the starting materials with the corresponding analytical method collected of the cocrystal. Data from a co crystal will be represented by an analytical response that is not simply a linear superposition of the starting materials. For example, x-ray powder diffraction (XRPD) may be used for such comparison and the XRPD pattern of a cocrystal will differ from that of a physical mixture of the starting materials. Single crystal studies can confirm solid-state structure. In a cocrystal, the compound and the coformers each possess unique lattice positions within the unit cell of the crystal lattice. Additionally, indexing may be used to confirm the presence of a single phase.

A single crystal structure is not necessary to characterize a cocrystal. Other solid-state analytical techniques may be used to characterize cocrystals. Crystallographic and spectroscopic properties of cocrystals can be analyzed with) (RFD, Raman spectroscopy, infrared spectroscopy, and solid-state NMR spectroscopy, among other techniques. Cocrystals often also exhibit distinct thermal behavior compared with other forms of the corresponding compound. Thermal behavior may be analyzed by such techniques as capillary melting point, thermogravimetric analysis (TGA), and differential scanning calorimetry (DSC) to name a few. These techniques can be used to identify and characterize the cocrystals.

For example, the entire XRPD pattern output from a diffractometer may be used to characterize a cocrystal. A smaller subset of such data, however, may also be suitable for characterizing a cocrystal. For example, a collection of one or more peaks from such a pattern may be used to characterize a cocrystal. Indeed, even a single XRPD peak may be used to characterize a cocrystal. Similarly, subsets of spectra of other techniques may be used alone or in combination with other analytical data to characterize cocrystals. In such examples of characterization as provided herein, in addition to the x-ray peak data, one also is able to provide the identity of the guest and host of the cocrystal and, often, their respective molar ratio as part of the characterization.

An XRPD pattern is an x-y graph with °2θ (diffraction angle) on the x-axis and intensity on the y-axis. These are the peaks which may be used to characterize a cocrystal. The peaks are usually represented and referred to by their position on the x-axis rather than the intensity of peaks on the y-axis because peak intensity can be particularly sensitive to sample orientation (see *Pharmaceutical Analysis*, Lee & Web, pp. 255-257 (2003)). Thus, intensity is not typically used by those skilled in the pharmaceutical arts to characterize cocrystals.

As with any data measurement, there is variability in x-ray powder diffraction data. In addition to the variability in peak intensity, there is also variability in the position of peaks on the x-axis. This variability can, however, typically be accounted for when reporting the positions of peaks for purposes of characterization. Such variability in the position of peaks along the x-axis derives from several sources. One comes from sample preparation. Samples of the same crystalline material, prepared under different conditions may yield slightly different diffractograms. Factors such as particle size, moisture content, solvent content, and orientation may all affect how a sample diffracts x-rays. Another source of variability comes from instrument parameters. Different x-ray instruments operate using different parameters and these may lead to slightly different diffraction patterns from the same crystalline cocrystal. Likewise, different software packages process x-ray data differently and this also leads to variability. These and other sources of variability are known to those of ordinary skill in the pharmaceutical arts.

Due to such sources of variability, it is common to recite x-ray diffraction peaks using the word "about" prior to the peak value in °2θ which presents the data to within 0.1 or 0.2

°2θ of the stated peak value depending on the circumstances. All x-ray powder diffraction peaks cited herein have are reported with a variability on the order of 0.2 °2θ and are intended to be reported with such a variability whenever disclosed herein whether the word "about" is present or not.

Raman spectroscopy and the related technique of infrared spectroscopy are additional techniques that may be used to characterize cocrystals together with or separately from x-ray powder diffraction. Raman and infrared peak intensity can be plotted versus "wavenumber." A wavenumber has the units of inverse centimeters ($cm^{-1}$). Wavenumbers are plotted on the x-axis intensity on the y-axis. As with x-ray powder diffraction plots, Raman and infrared peaks are recorded by reference to their x-axis (wavenumber) position rather than their intensity. Variation in the position of Raman and infrared peaks also exists and may be due to sample conditions as well as data collection and processing. The typical variability in such spectra reported herein is on the order plus or minus 2.0 $cm^{-1}$. Thus, the use of the word "about" when referencing Raman and infrared peaks is meant to include this variability and all Raman peaks disclosed herein are intended to be reported with such variability whether the word "about" is present or not.

Thermal methods are another typical technique to characterize cocrystals. Different cocrystals of the same compound often melt at different temperatures. Variability also exists in thermal measurements, such as DSC, and may also be indicative of sample purity. Melting point, DSC, and hot stage microscopy, alone or in combination with techniques such as x-ray powder diffraction, Raman spectroscopy, infrared spectroscopy or some combination thereof, may be used to characterize cocrystals.

As with any analytical technique, melting points determinations are also subject to variability. Common sources of variability, in addition to instrumental variability, are due to colligative properties such as the presence of other cocrystals or other impurities within a sample whose melting point is being measured.

SUMMARY

In one aspect of the disclosure, a co crystal of progesterone with a coformer which contains a six-membered aromatic ring having at least one substituent possessing a carbonyl functionality is provided. In another aspect of the disclosure, a cocrystal of progesterone with a coformer selected from vanillic acid, benzoic acid, salicylic acid, cinnamic acid, or vanillin is provided.

In a further aspect of the disclosure, the invention is directed to a cocrystal of progesterone and vanillic acid in the molar ratio of 1:1. In another aspect of the invention, the disclosure is directed to a hemihydrate cocrystal of progesterone and benzoic acid in the molar ratio of 2:1. In a further aspect of the disclosure, the invention is directed to a cocrystal of progesterone and salicylic acid in the molar ratio of 1:1. In yet a further aspect of the disclosure, the invention is directed to a cocrystal of progesterone and salicylic acid in the molar ratio of 2:1. In an additional aspect of the disclosure, the invention is directed to a cocrystal of progesterone and cinnamic acid. In another aspect of the invention, the disclosure is directed to a cocrystal of progesterone and vanillin in the molar ratio of 2:1.

DESCRIPTION

Figure 32:
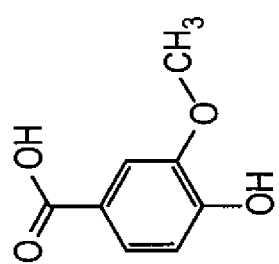
FIG. 32 shows the structure of conformer.
Figure 31:
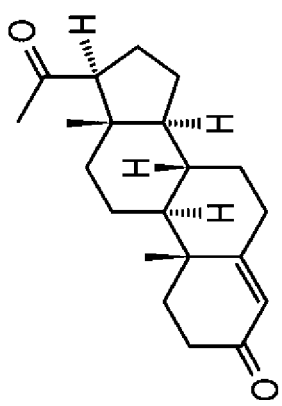
FIG. 31 shows the structure of progesterone.

In one embodiment of the invention, a cocrystal of progesterone:vanillic acid in a molar ratio of 1:1 (Cocrystal 1) is disclosed. The structure of Cocrystal 1 is set forth in FIG. 1. The structure of coformer is shown in FIG. 32.

Figure 2:
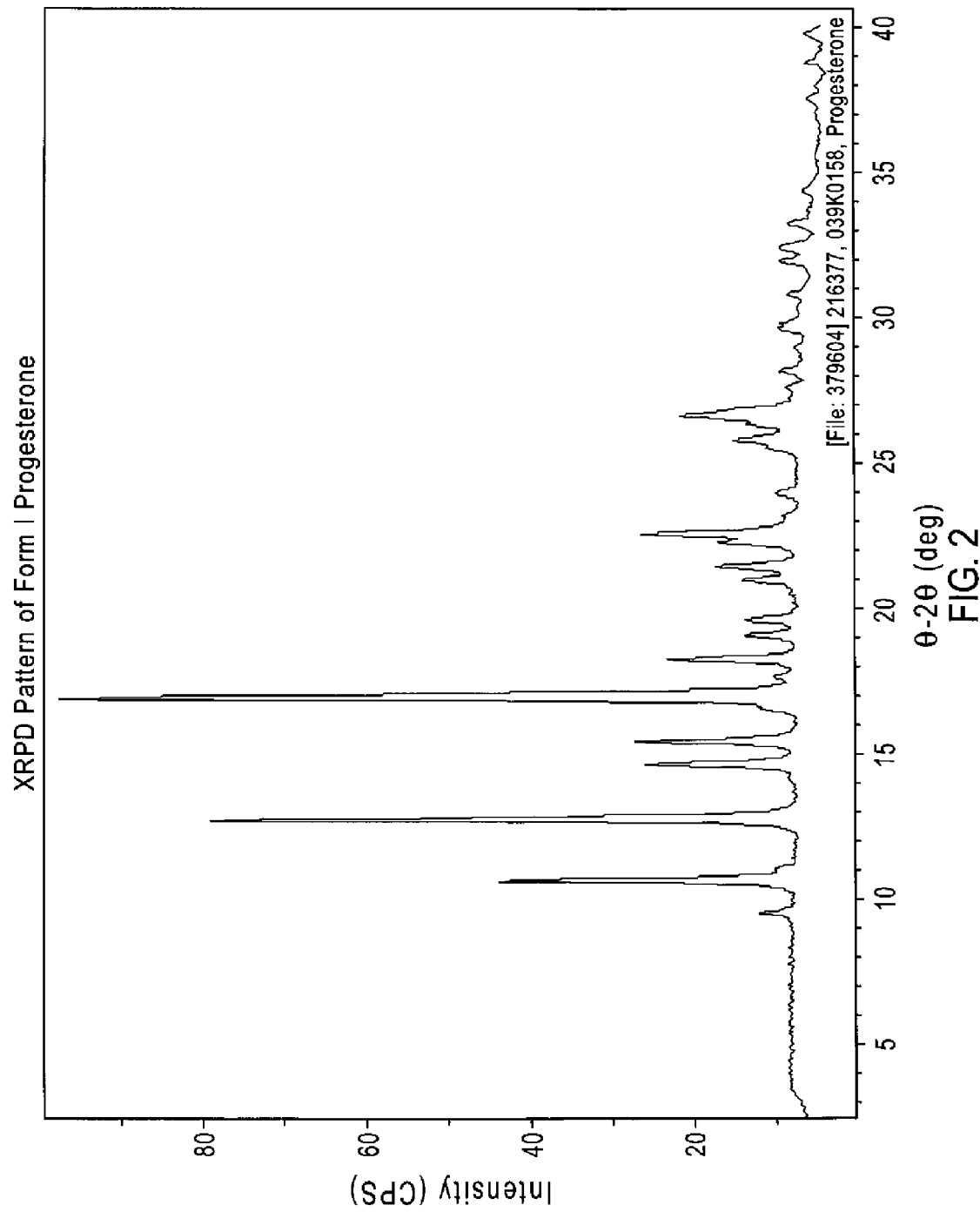
FIG. 2 is an XRPD pattern of Form I of progesterone
Figure 3:
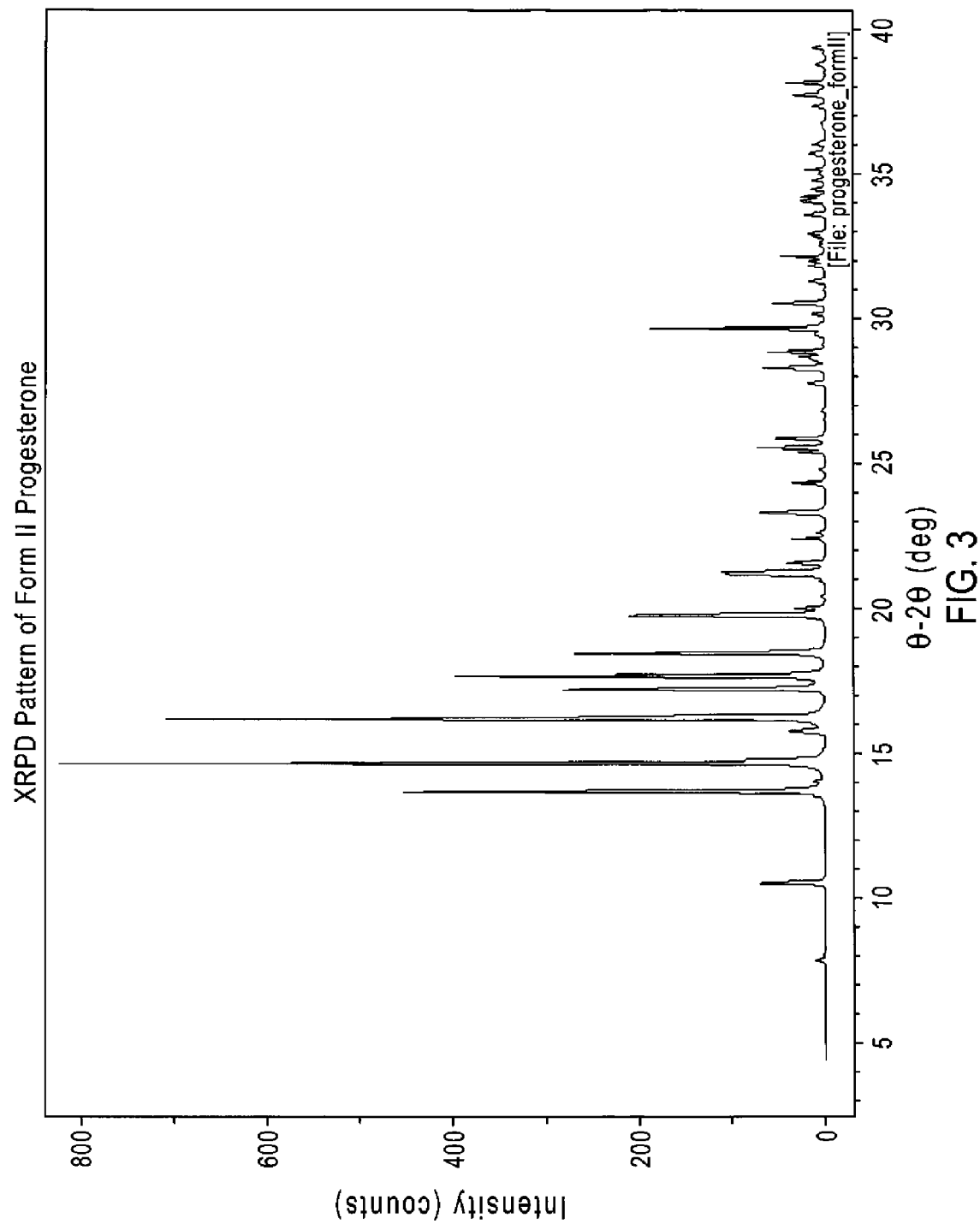
FIG. 3 is an XRPD pattern of Form II of progesterone from the literature.
Figure 4:
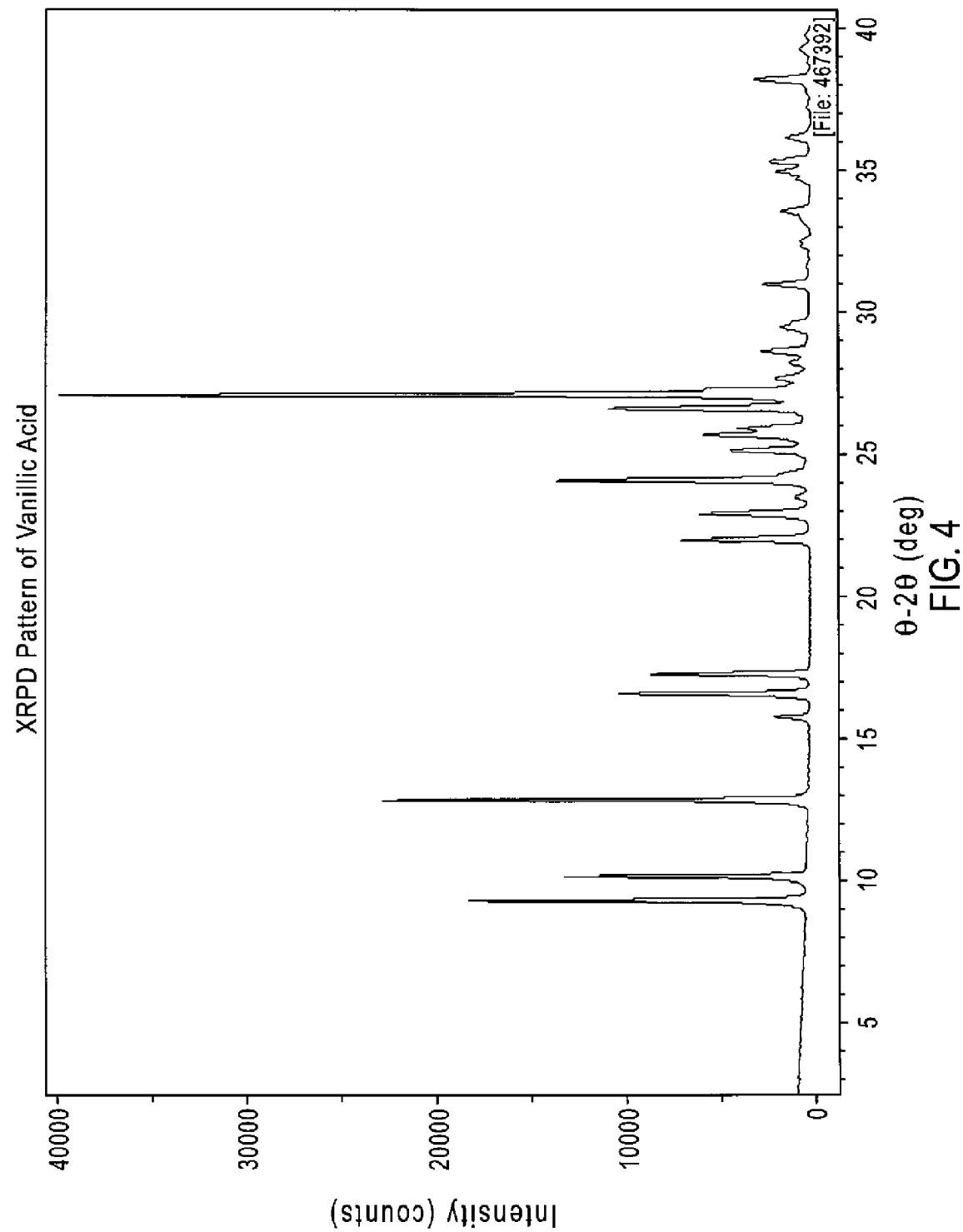
FIG. 4 is an XRPD pattern of vanillic acid.

The XRPD pattern corresponding to the progesterone form I starting material used herein is in FIG. 2. The XRPD pattern of metastable form II taken from the literature of progesterone is provided for comparison in FIG. 3. The XRPD pattern of the vanillic acid starting material used herein can be found in FIG. 4.

Figure 1:
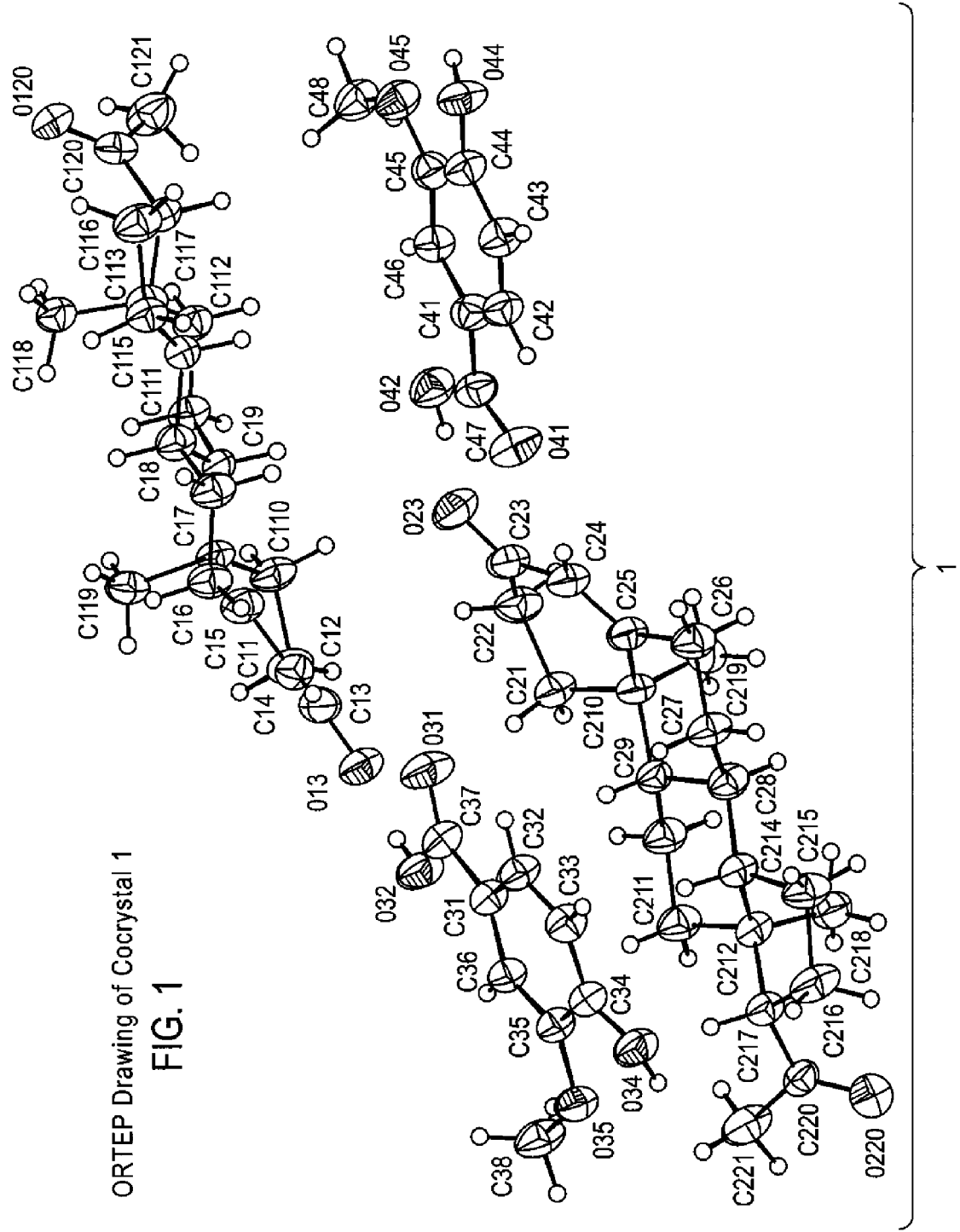
FIG. 1 is an ORTEP drawing of Cocrystal 1.
Figure 5:
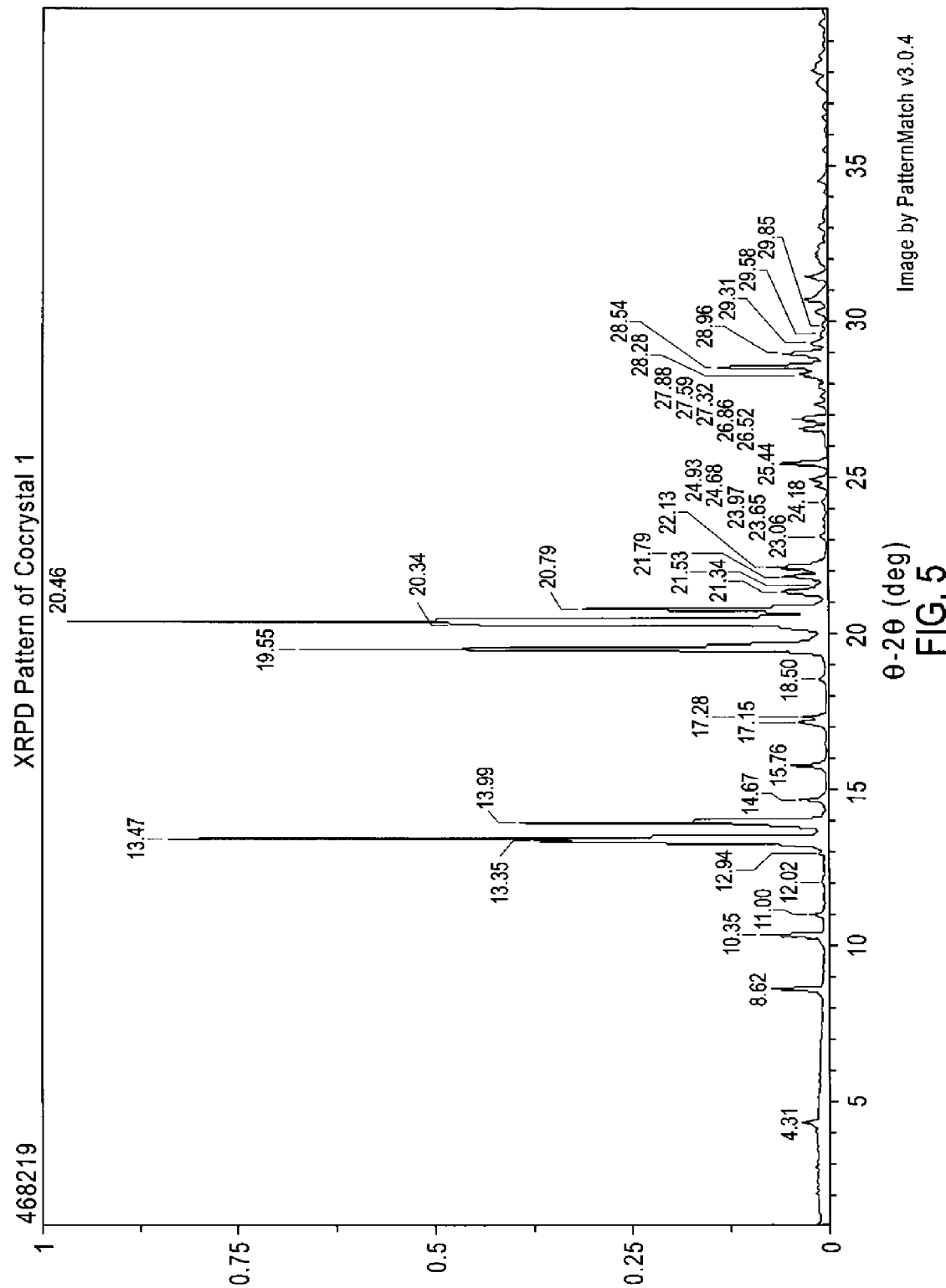
FIG. 5 is an XRPD pattern of Cocrystal 1.

The XRPD pattern corresponding to Cocrystal 1 is represented by FIG. 5. As can be readily determined, the XPRD pattern of FIG. 5 differs those of FIGS. 2 and 4 and is not merely a linear superposition of the patterns as confirmed by the single crystal structure which is represented in FIG. 1, the parameters for which are set forth in Table 1.

TABLE 1

CRYSTAL DATA AND DATA COLLECTION PARAMETERS FOR Cocrystal 1

| | |
|---|---|
| formula | $C_{29}H_{38}O_6$ |
| formula weight | 482.62 |

TABLE 1-continued

CRYSTAL DATA AND DATA COLLECTION PARAMETERS FOR Cocrystal 1

| | |
|---|---|
| space group | P2$_1$ (No. 4) |
| a, Å | 7.1875(4) |
| b, Å | 40.8726(18) |
| c, Å | 9.3001(4) |
| β, deg | 112.357(4) |
| V, Å$^3$ | 2526.7(2) |
| Z | 4 |
| d$_{calc}$, g cm$^{-3}$ | 1.269 |
| crystal dimensions, mm | 0.20 × 0.20 × 0.12 |
| temperature, K | 150 |
| radiation (wavelength, Å) | Cu K$_\alpha$ (1.54184) |
| monochromator | confocal optics |
| linear abs coef, mm$^{-1}$ | 0.705 |
| absorption correction applied | empirical |
| transmission factors: min, max | 0.81, 0.92 |
| diffractometer | Rigaku RAPID-II |
| h, k, l range | −8 to 8 −49 to 49 −11 to 11 |
| 2Θ range, deg | 4.32-140.18 |
| mosaicity, deg | 0.74 |
| programs used | SHELXTL |
| F$_{000}$ | 1040.0 |
| weighting 1/[σ$^2$(Fo$^2$) + (0.1674P)$^2$ + 2.2275P] where P = (Fo$^2$ + 2Fc$^2$)/3 | |
| data collected | 23094 |
| unique data | 8024 |
| R$_{int}$ | 0.084 |
| data used in refinement | 8024 |
| cutoff used in R-factor calculations | F$_o^2$ > 2.0 σ (F$_o^2$) |
| data with I > 2.0 σ (I) | 7780 |
| number of variables | 644 |
| largest shift/esd in final cycle | 0.00 |
| R(F$_o$) [Σ |Fo − Fc|/Σ Fo] | 0.081 |
| R$_w$(F$_o^2$) [SQRT (Σ w (Fo$^2$ − Fc$^2$)$^2$/Σ w (Fo$^2$)$^2$)] | 0.235 |
| goodness of fit | 1.041 |
| absolute structure determination | Flack parameter (0.3(3)) Hooft parameter (0.21(5)) Friedel Coverage 81% |

A pattern substantially the same as the pattern of FIG. 5 may be used to characterize Cocrystal 1. A smaller subset of the peaks identified in FIG. 5 may be used to characterize Cocrystal 1. For example, anyone or more of the peaks at about 8.6, 10.4, 13.4, 13.5, 14.0, 19.6, 20.5, 20.8, or 28.5 °2θ may be used to characterize Cocrystal 1.

Figure 6:
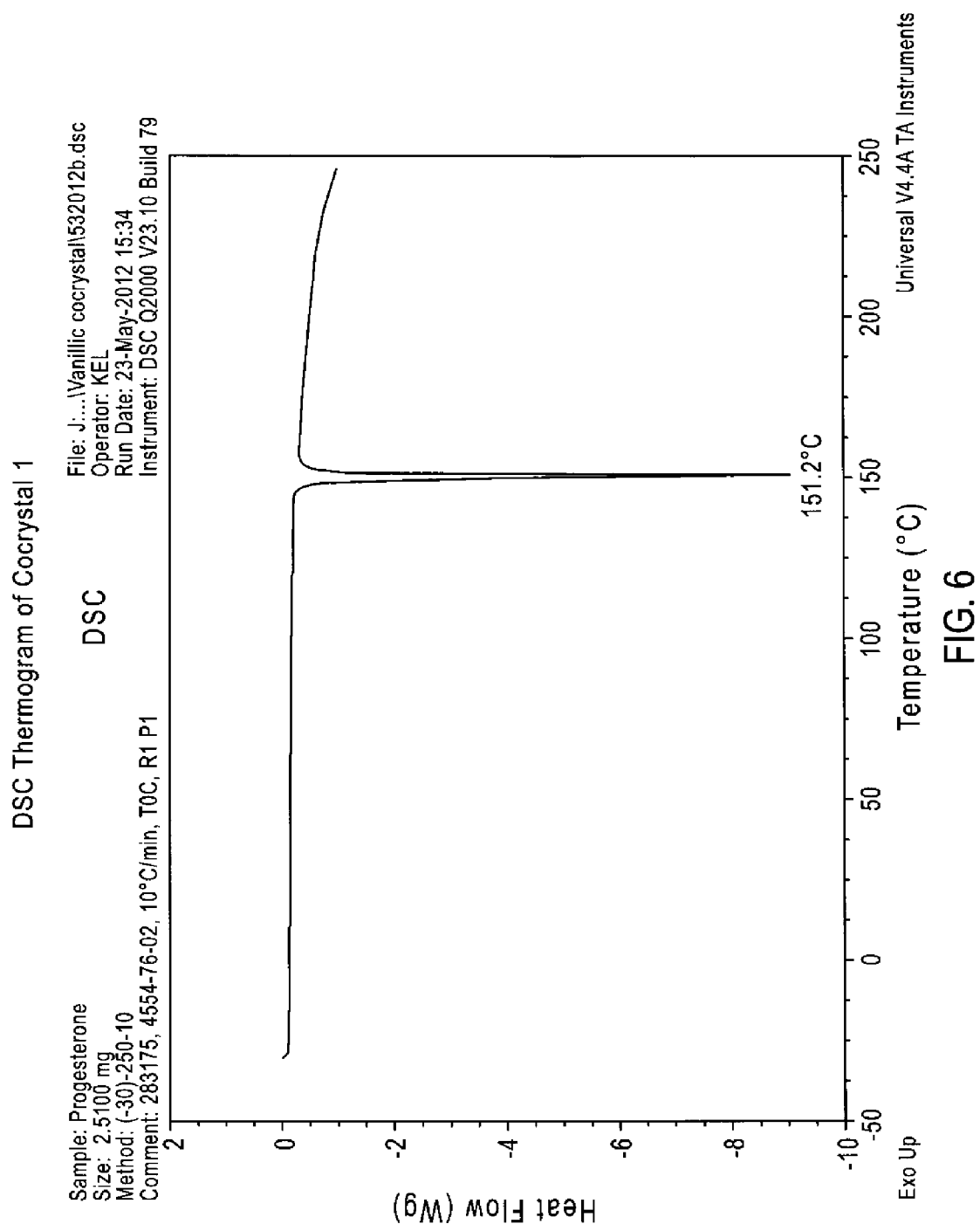
FIG. 6 is a DSC thermogram of Cocrystal 1.

Cocrystal 1 may be characterized by its thermal characteristics. For example, FIG. 6 is a DSC thermogram of Cocrystal 1 and it exhibits an endotherm at about 151° C. under the conditions set forth herein for DSC for the thermogram in FIG. 6. Cocrystal 1 may be characterized by DSC alone or in combination with XRPD diffraction pattern or one or more of the peaks set forth herein.

Figure 7:
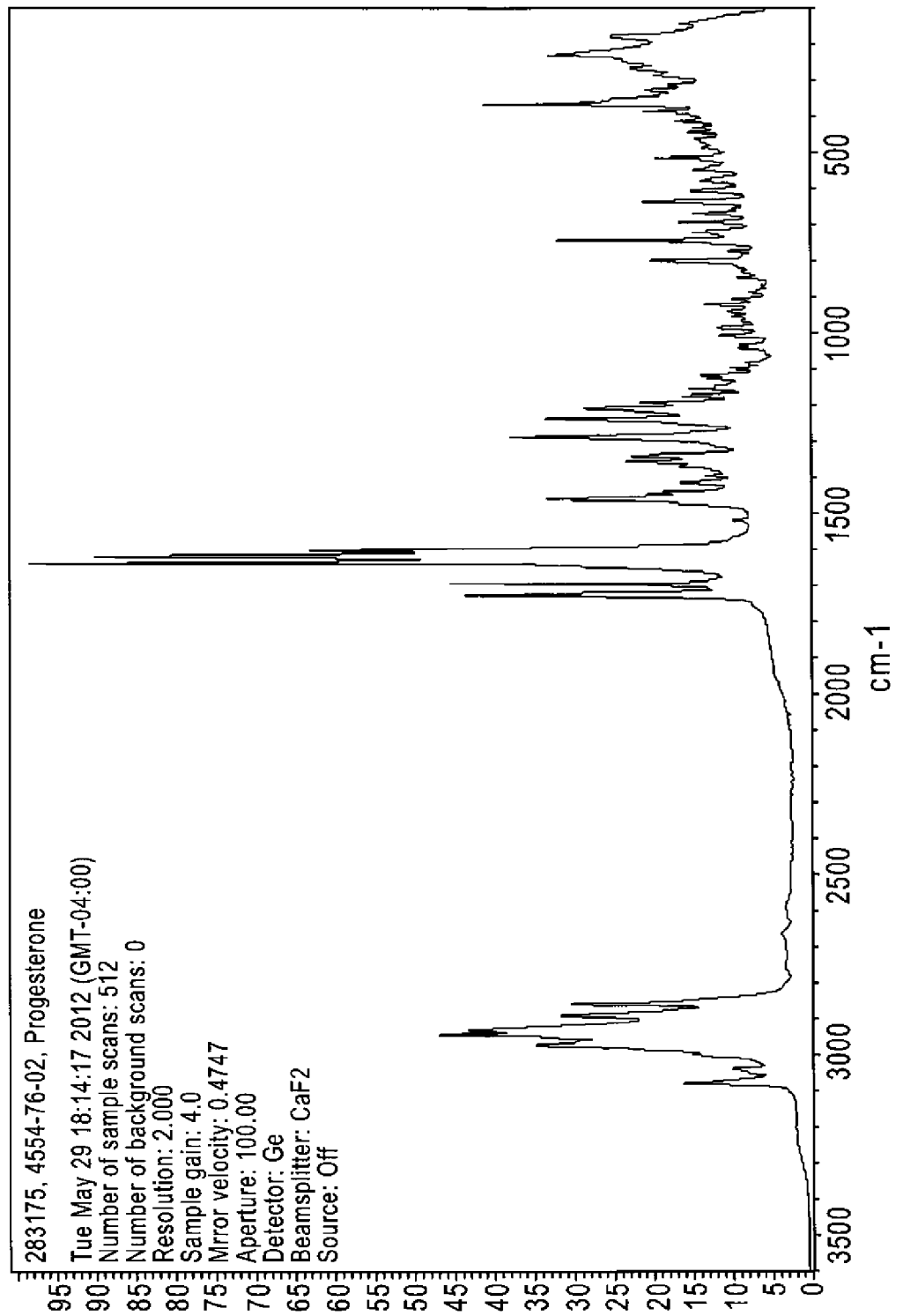
FIG. 7 is a Raman spectrum of Cocrystal 1.

Cocrystal 1 may be characterized by the Raman spectrum in FIG. 7. When considering just Raman spectroscopy, the entire Rama spectrum may be used to characterized Cocrystal 1 or a subset thereof. For example, any one of the peaks at about 1596, 1610, 1629, 1690, or 1720 cm$^{-1}$ or others may be used alone or in combination to characterize Cocrystal 1.

Cocrystal 1 may be characterized by one or more of the Raman, DSC, and x-ray techniques as set forth herein. For example, Cocrystal 1 may be characterized by a peak at about 8.6 °2θ and DSC onset temperature of about 151° C. Further, a Raman peak at about 1629 cm$^{-1}$ may be used to characterize Cocrystal 1.

Powder dissolution data for the progesterone-vanillic acid cocrystal were obtained and showed an increase in dissolution rate and sustained progesterone concentration over time compared to commercially available progesterone.

Figure 33:
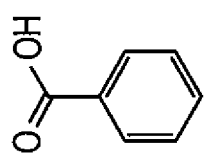
FIG. 33 shows structure of benzoic acid.

In another embodiment of the invention, a cocrystal of progesterone:benzoic acid hemihydrate in a molar ratio of 2:1 as a hemihydrate (Cocrystal 2) is disclosed. The structure of Cocrystal 2 is set forth in FIG. 8. The structure of benzoic acid is shown in FIG. 33.

Figure 9:
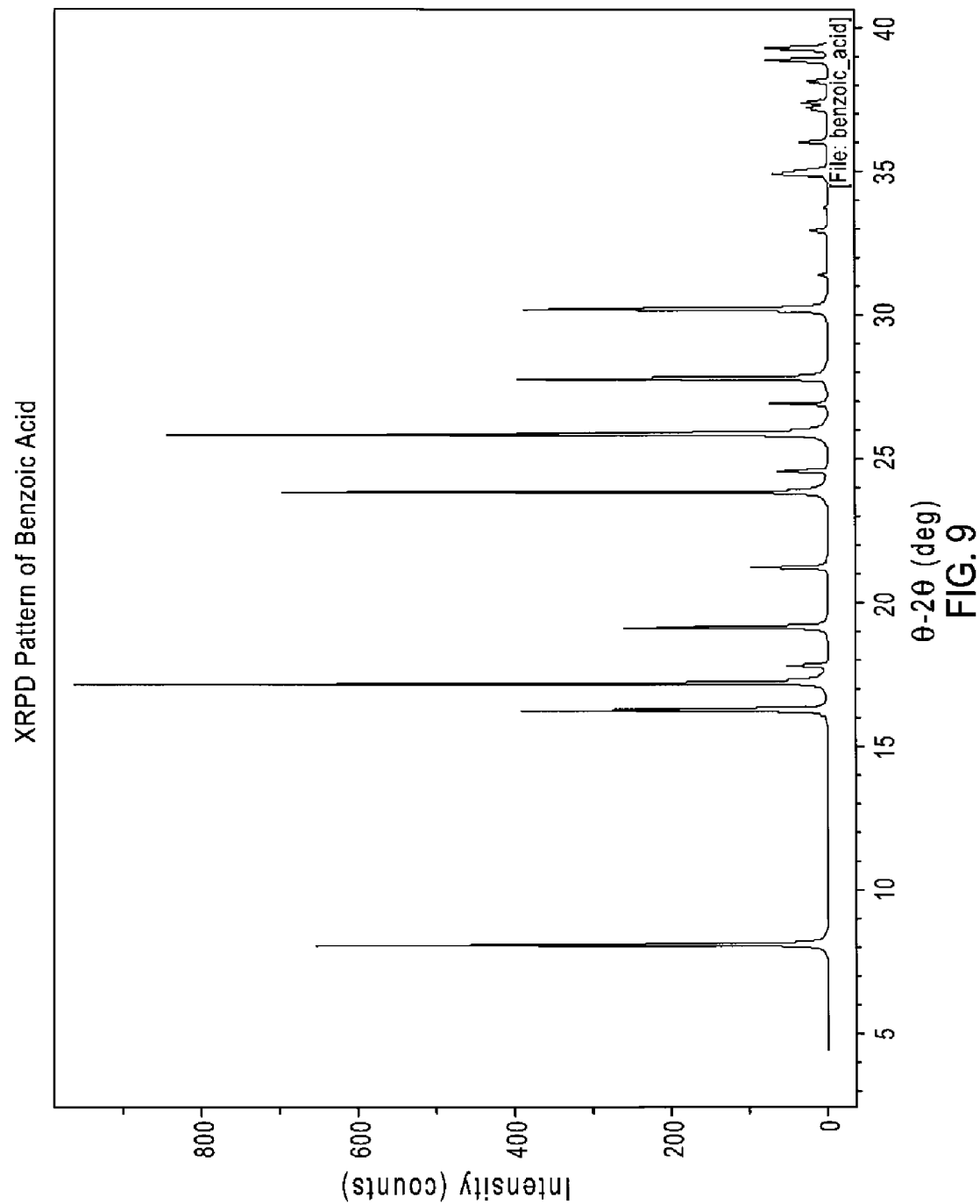
FIG. 9 is an XRPD pattern of benzoic acid from the literature.

The XRPD pattern corresponding to the progesterone form I starting material used herein is in FIG. 2. The XRPD pattern of benzoic acid taken from the literature can be found in FIG. 9.

Figure 8:
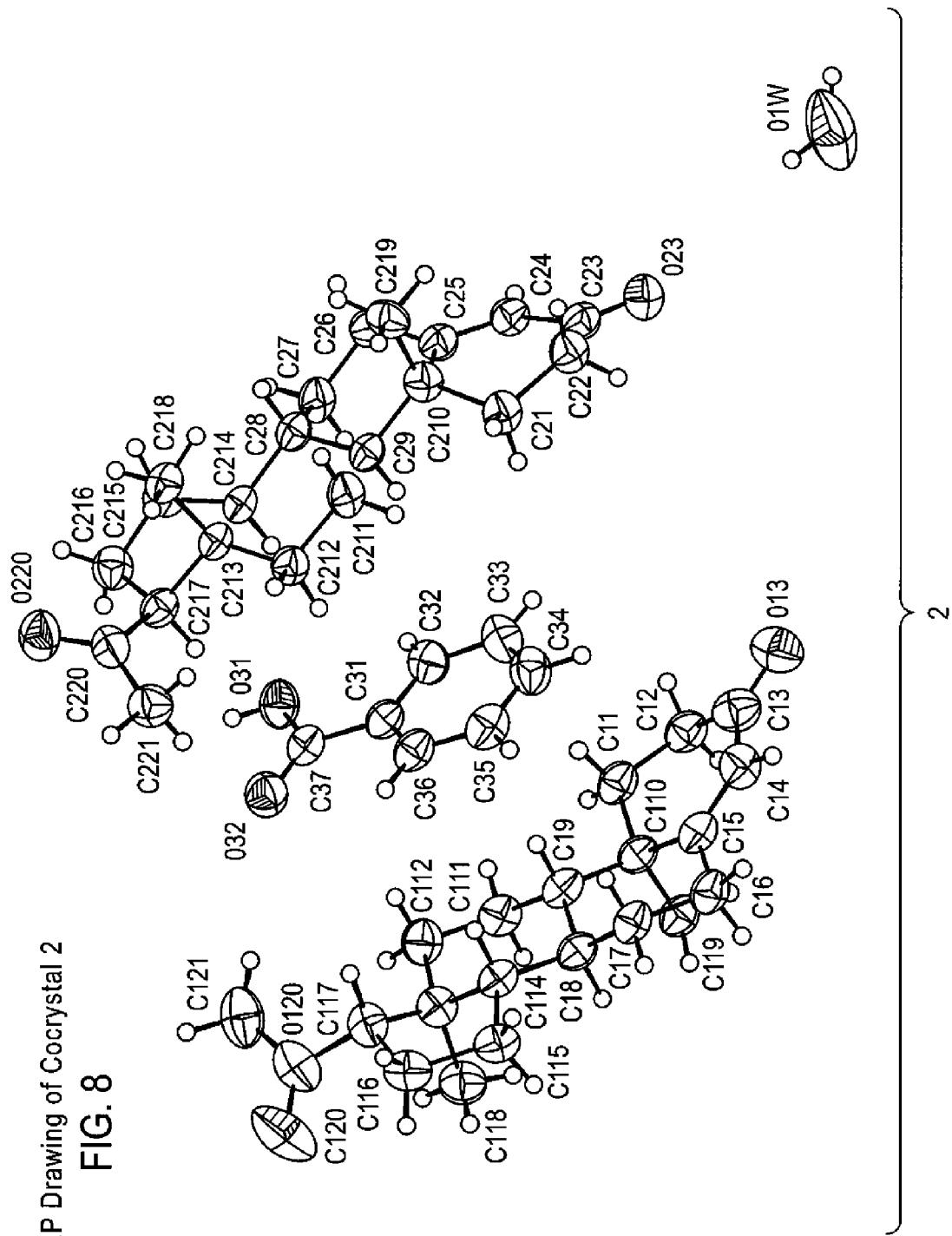
FIG. 8 is an ORTEP drawing of Cocrystal 2.
Figure 10:
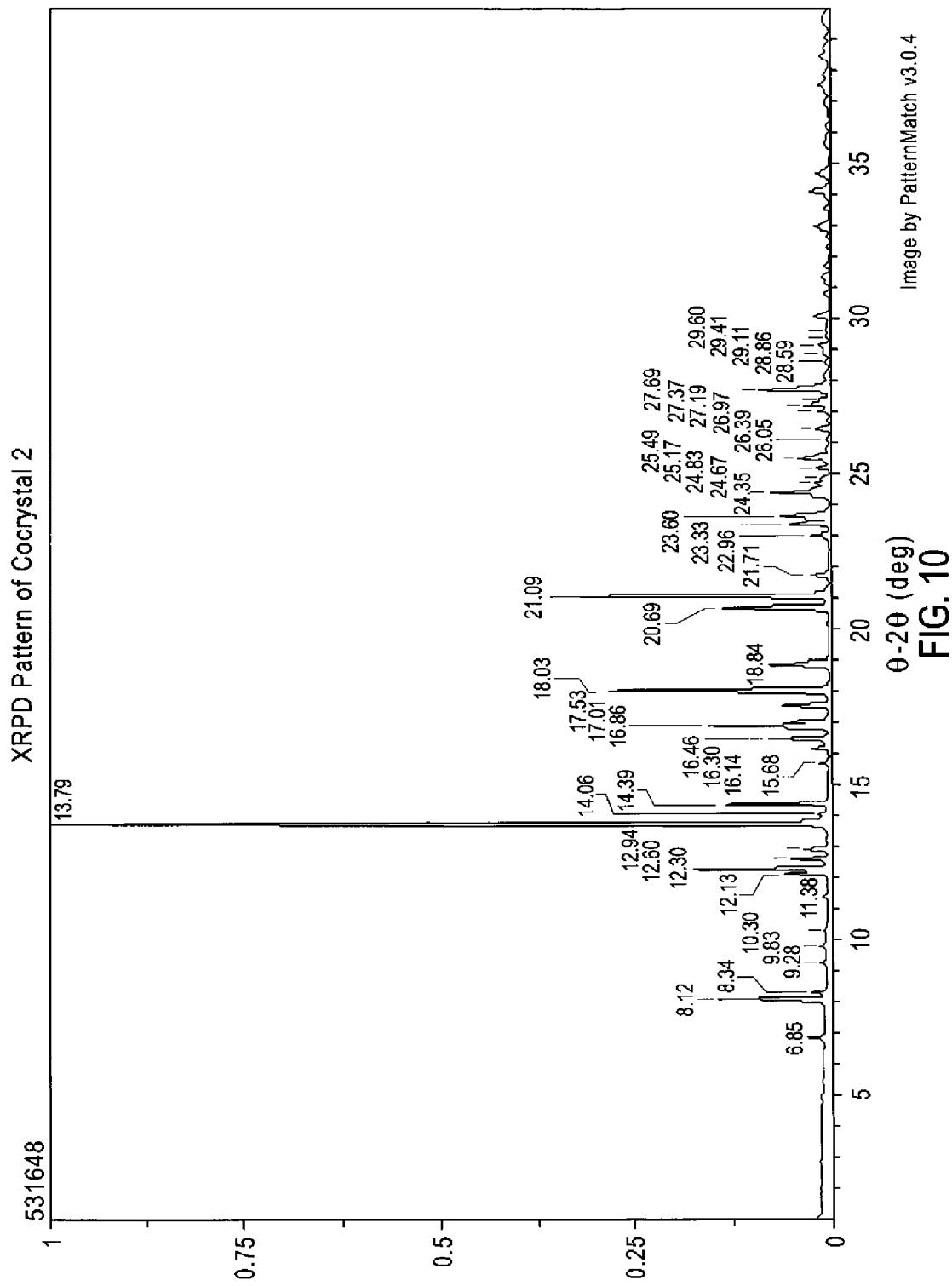
FIG. 10 is an XRPD pattern of Cocrystal 2.

The XRPD pattern corresponding to Cocrystal 2 is represented by FIG. 10. As can be readily determined, the XPRD pattern of FIG. 5 differs from those of FIGS. 2 and 9 and is not merely a linear superposition of the patterns as confirmed by the single crystal structure which is represented in FIG. 8, the parameters for which are set forth in Table 2.

TABLE 2

CRYSTAL DATA AND DATA COLLECTION PARAMETERS FOR Cocrystal 2

| | |
|---|---|
| formula | C$_{49}$H$_{67}$O$_{6.50}$ |
| formula weight | 760.08 |
| space group | C2 (No. 5) |
| a, Å | 21.8930(11) |
| b, Å | 7.5667(5) |
| c, Å | 25.6398(17) |
| β, deg | 98.151(5) |
| V, Å$^3$ | 4204.5(4) |
| Z | 4 |
| d$_{calc}$, g cm$^{-3}$ | 1.201 |
| crystal dimensions, mm | 0.20 × 0.08 × 0.02 |
| temperature, K | 150 |
| radiation (wavelength, Å) | Cu K$_\alpha$ (1.54184) |
| monochromator | confocal optics |
| linear abs coef, mm$^{-1}$ | 0.611 |
| absorption correction applied | empirical |
| transmission factors: min, max | 0.88, 0.99 |
| diffractometer | Rigaku RAPID-II |
| h, k, l range | −26 to 26 −8 to 9 −31 to 30 |
| 2Θ range, deg | 6.97-140.36 |
| mosaicity, deg | 0.82 |
| programs used | SHELXTL |
| F$_{000}$ | 1668.0 |
| weighting 1/[σ$^2$(Fo$^2$) + (0.1205P)$^2$ + 2.7195P] where P = (Fo$^2$ + 2Fc$^2$)/3 | |
| data collected | 23573 |
| unique data | 7183 |
| R$_{int}$ | 0.075 |
| data used in refinement | 7183 |
| cutoff used in R-factor calculations | F$_o^2$ > 2.0 σ (F$_o^2$) |
| data with I > 2.0 σ (I) | 6794 |
| number of variables | 515 |
| largest shift/esd in final cycle | 0.00 |
| R(F$_o$) [Σ |Fo − Fc|/Σ Fo] | 0.066 |
| R$_w$(F$_o^2$) [SQRT (Σ w (Fo$^2$ − Fc$^2$)$^2$/Σ w (Fo$^2$)$^2$)] | 0.186 |
| goodness of fit | 1.087 |
| absolute structure determination | Flack parameter (−0.1(3)) Hooft parameter (−0.04(6)) Friedel Coverage 81% |

A pattern substantially the same as the pattern of FIG. 10 may be used to characterize Cocrystal 2. A smaller subset of the peaks identified in FIG. 10 may be used to characterize Cocrystal 2. For example, anyone or more of the peaks at about 8.1, 12.3, 13.8, 14.4, 16.9, 18.0, 20.7, or 21.1 °2θ may be used to characterize Cocrystal 2.

Figure 11:
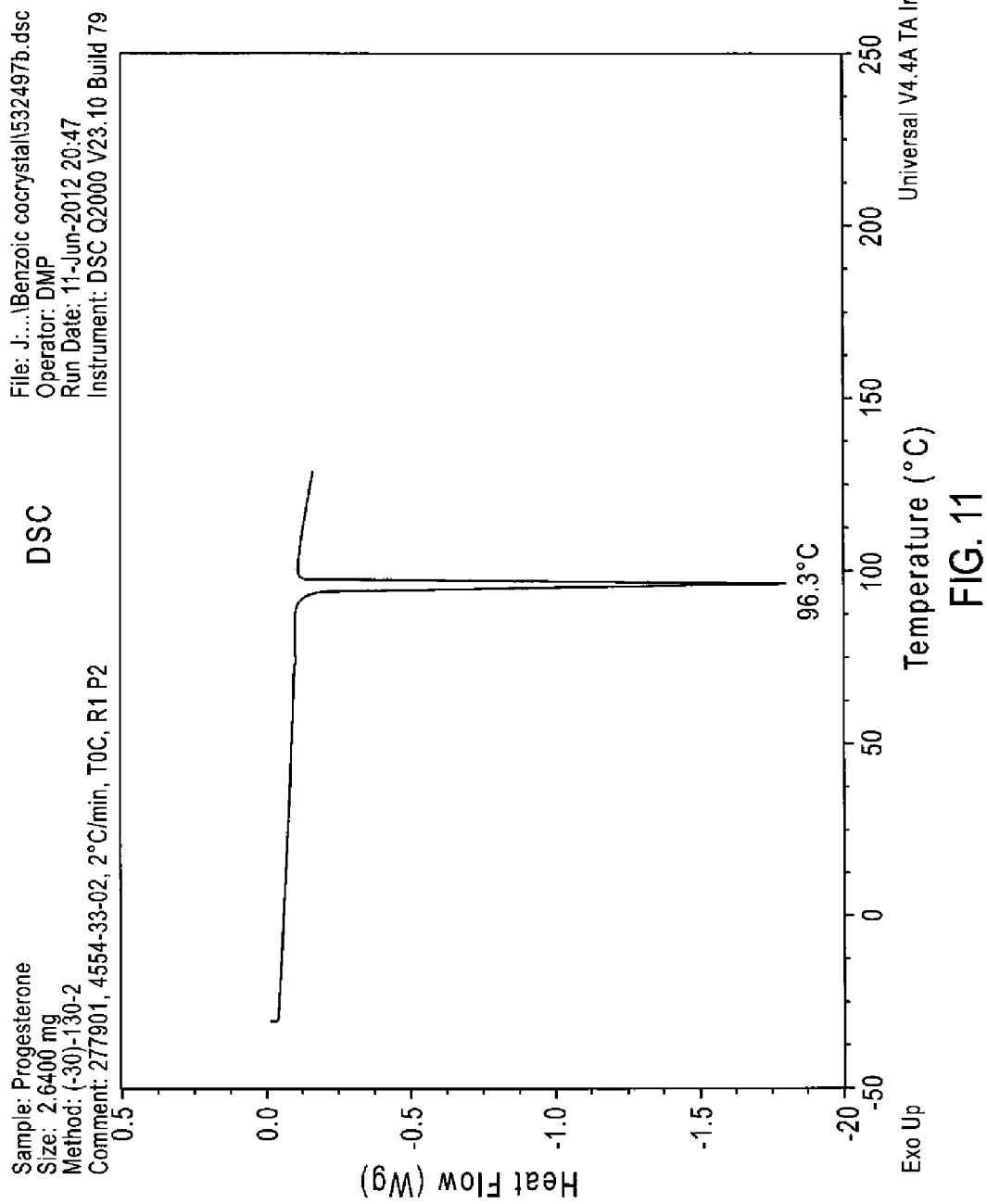
FIG. 11 is a DSC Thermogram of Cocrystal 2.

Cocrystal 2 may be characterized by its thermal characteristics. For example, FIG. 11 is a DSC thermogram of Cocrystal 2 and it exhibits an endotherm at about 96° C. under the conditions set forth herein for DSC in FIG. 11. Cocrystal may be characterized by DSC alone or in combination with XRPD diffraction pattern or one or more of the peaks set forth herein.

Figure 12:
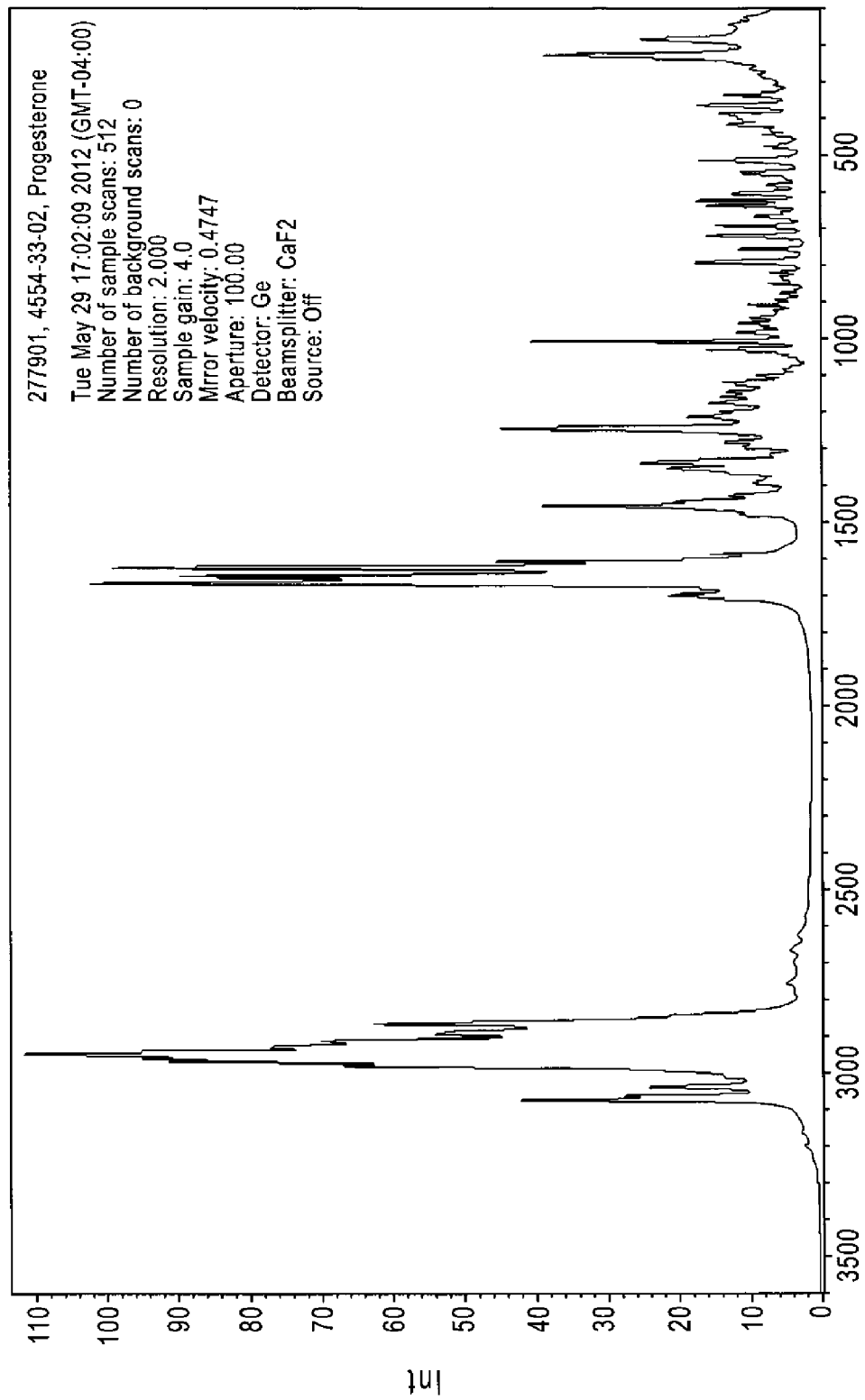
FIG. 12 is a Raman spectrum of Cocrystal 2.

Cocrystal 2 may be characterized by the Raman spectrum in FIG. 12. When considering just Raman spectroscopy, the entire Rama spectrum may be used to characterized Cocrystal 2 or a subset thereof. For example, anyone of the peaks at about 160, 1613, 1640, 1658 or 2943 cm$^{-1}$ or others may be used alone or in combination to characterize Cocrystal 2.

Cocrystal 2 may be characterized by one or more of the Raman, DSC, and x-ray techniques as set forth herein. For example, Cocrystal 2 maybe characterized by a peak at 8.1 or 13.8 and a DSC onset temperature of about 96° C. Further, a Raman peak at about 1658 cm$^{-1}$ may be used to characterize Cocrystal 2.

Figure 34:
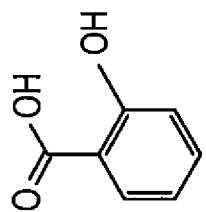
FIG. 34 shows the structure of salicylic acid.

In another embodiment of the invention, a cocrystal of progesterone:salicylic acid in a molar ratio of 1:1 (Cocrystal 3) is disclosed. The structure of salicylic acid is shown in FIG. 34.

Figure 13:
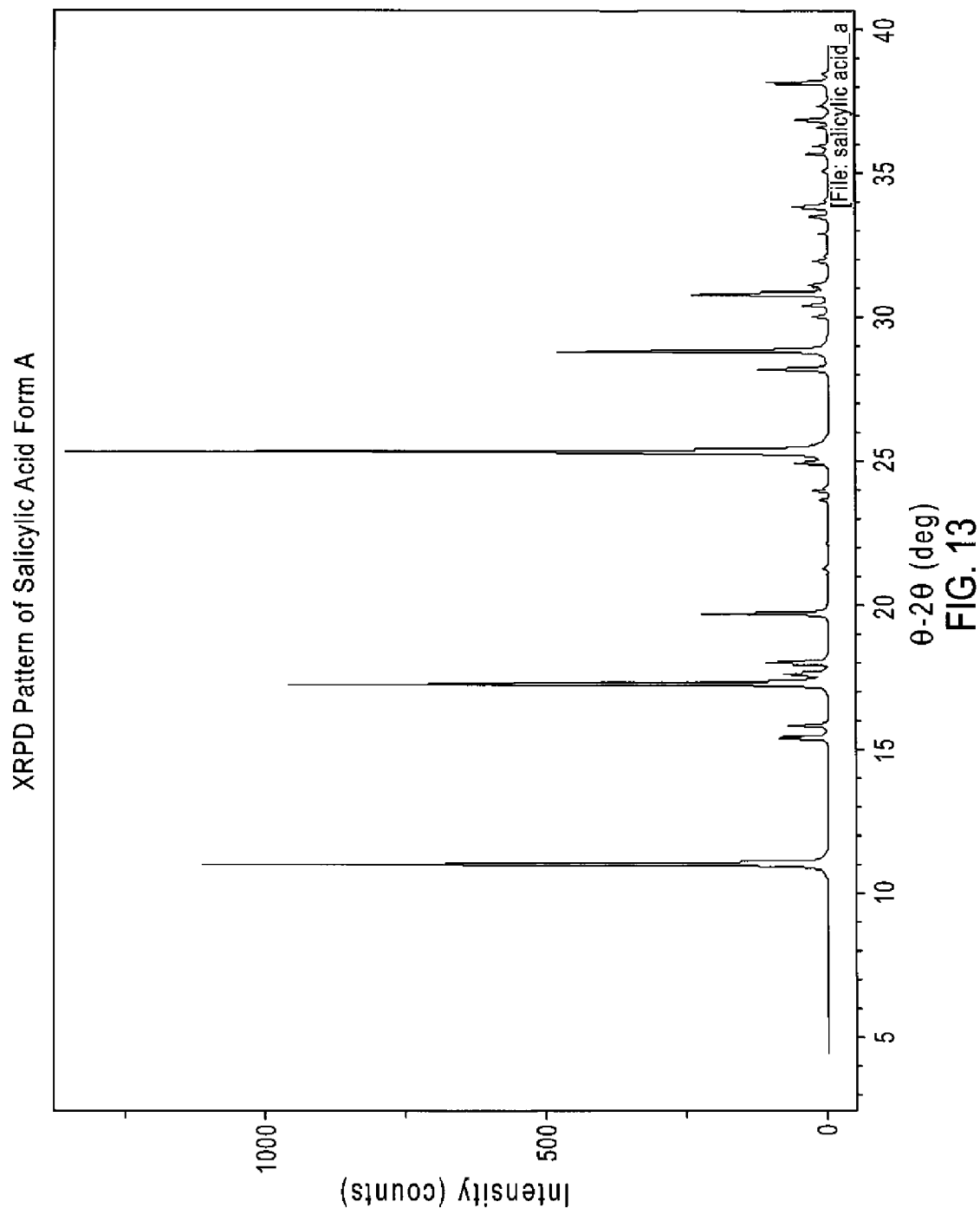
FIG. 13 is an XRPD pattern of salicylic acid from the literature.

The XRPD pattern corresponding to the progesterone form I starting material used herein is in FIG. 2. The XRPD pattern of the salicylic acid from the literature starting can be found in FIG. 13.

Figure 14:
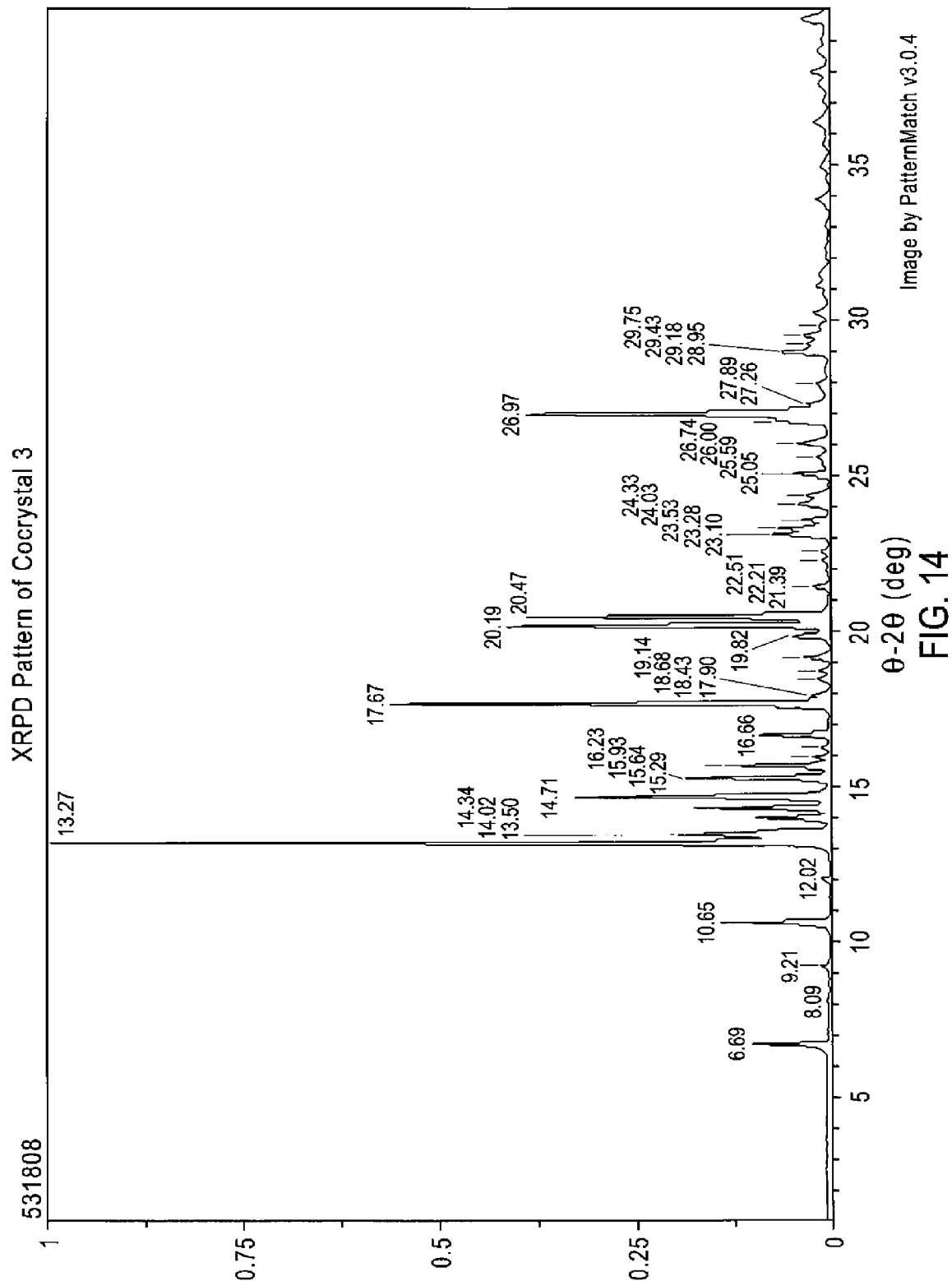
FIG. 14 is an XRPD pattern of Cocrystal 3.

The XRPD pattern corresponding to Cocrystal 3 is represented by FIG. 14. As can be readily determined, the XPRD pattern of FIG. 14 differs from those of FIGS. 2 and 13 and is not merely a linear superposition of the patterns. Stoichiometry of the cocrystal was verified by solution-state $^1$H NMR spectroscopy.

A pattern substantially the same as the pattern of FIG. 14 may be used to characterize Cocrystal 3. A smaller subset of the peaks identified in FIG. 14 may be used to characterize Cocrystal 3. For example, anyone or more of the peaks at about 6.7, 10.7, 13.3, 13.5, 14.3, 14.7, 17.7, 20.2, 20.5, or 27.0 °2θ may be used to characterize Cocrystal 3.

Figure 15:
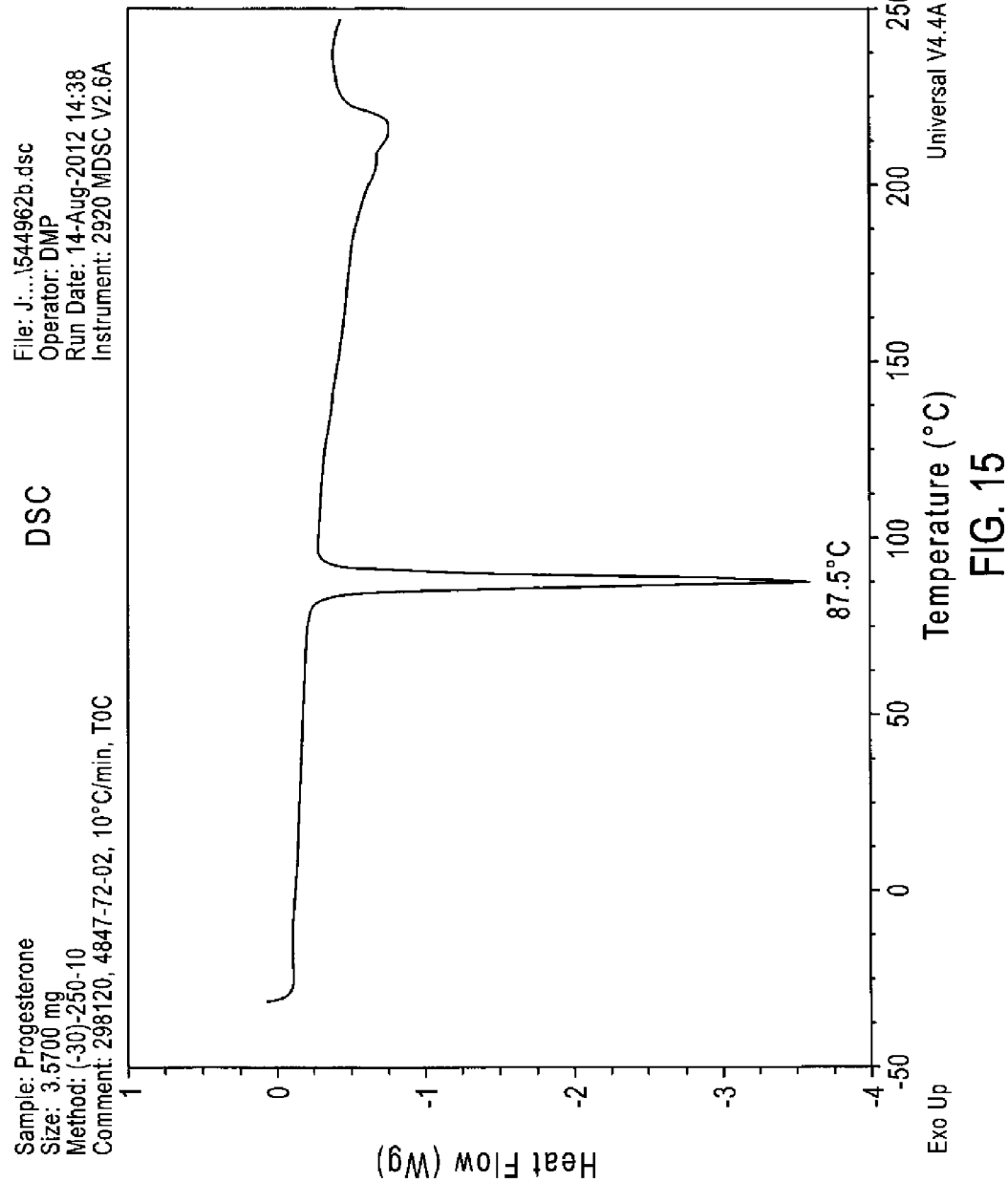
FIG. 15 is a DSC thermogram of Cocrystal 3.

Cocrystal 3 may be characterized by its thermal characteristics. For example, FIG. 15 is a DSC thermogram of Cocrystal 3 and it exhibits an endotherm at about 88° C. under the conditions set forth herein for DSC in FIG. 15. Cocrystal 3 may be characterized by DSC alone or in combination with XRPD diffraction pattern or one or more of the peaks set forth herein.

Figure 16:
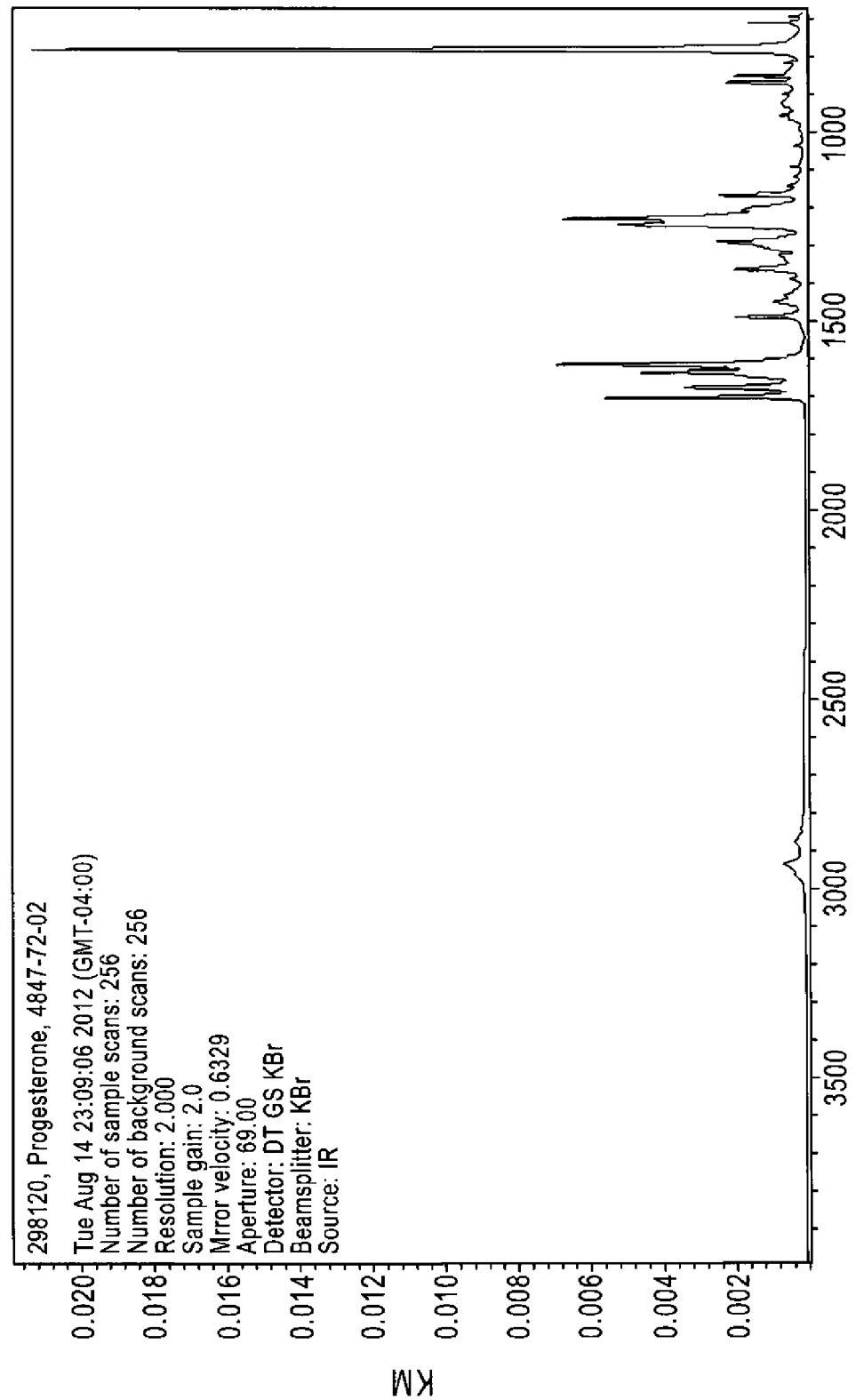
FIG. 16 is an FT-infrared spectrum of Cocrystal 3.

Cocrystal 3 may be characterized by the infrared spectrum in FIG. 16. When considering just infrared spectroscopy, the entire infrared spectrum may be used to characterized Cocrystal 3 or a subset thereof. For example, anyone of the peaks at 773, 1162, or 1609 cm$^{-1}$ or others may be used alone or in combination to characterize Cocrystal 3.

Figure 26:
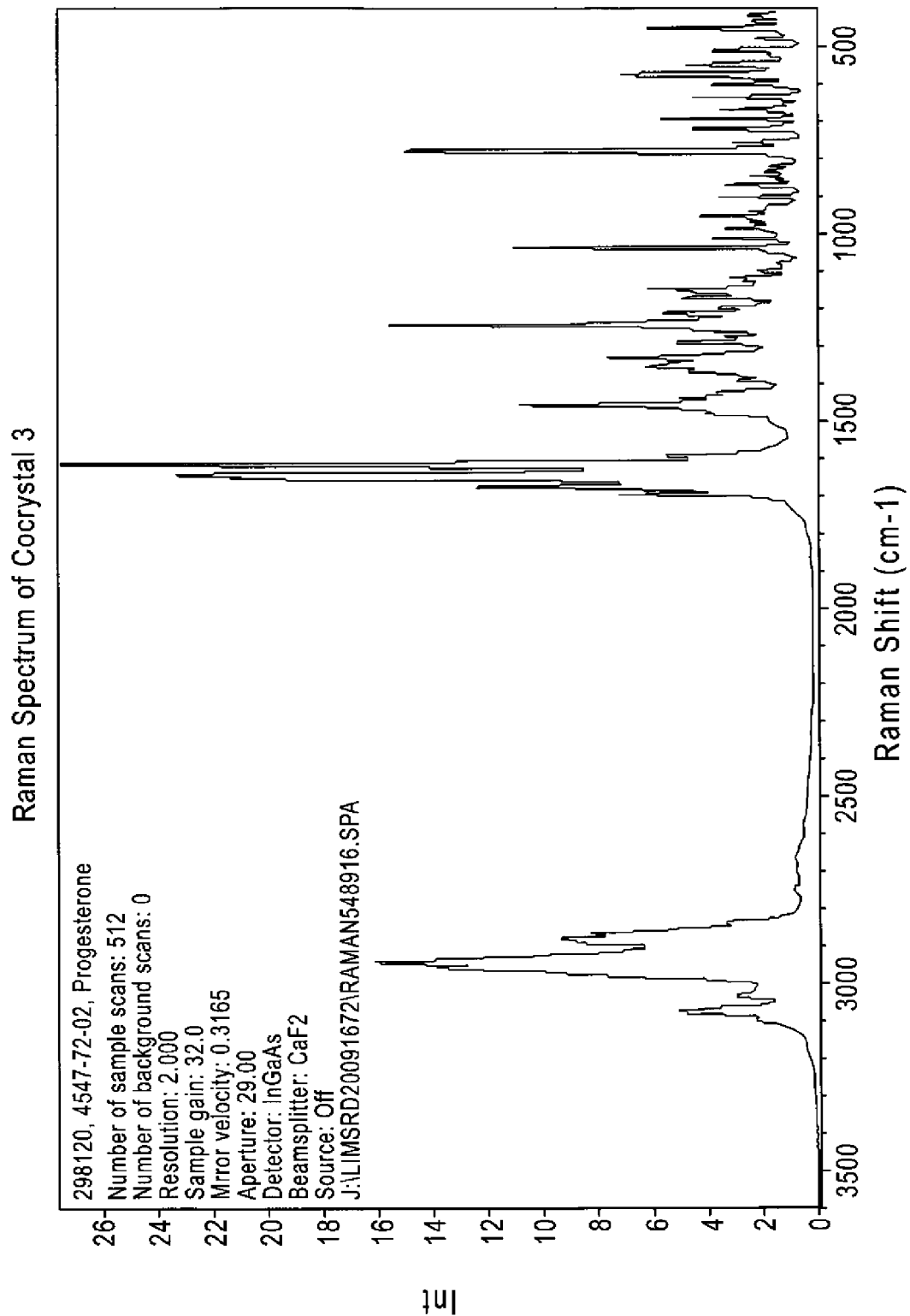
FIG. 26 is a Raman spectrum of Cocrystal 3.

Cocrystal 3 may be characterized by the Raman spectrum in FIG. 26. When considering just Raman spectroscopy, the entire Rama spectrum may be used to characterized Cocrystal 3 or a subset thereof. For example, anyone of the peaks at about 770, 1235, 1608, 1636, 1644, or others may be used alone or in combination to characterize Cocrystal 3.

Cocrystal 3 may be characterized by one or more of the infrared, DSC, Raman, and x-ray techniques as set forth herein. For example, Cocrystal 3 may be characterized by a peak at about 10.7 °2θ, a DSC onset temperature of about 88° C. Further, an infrared peak at about 773 cm$^{-1}$ may be used to characterize Cocrystal 3. Further, a Raman peak at about 1608 cm$^{-1}$ may be used to characterize Cocrystal 3.

Figure 17:
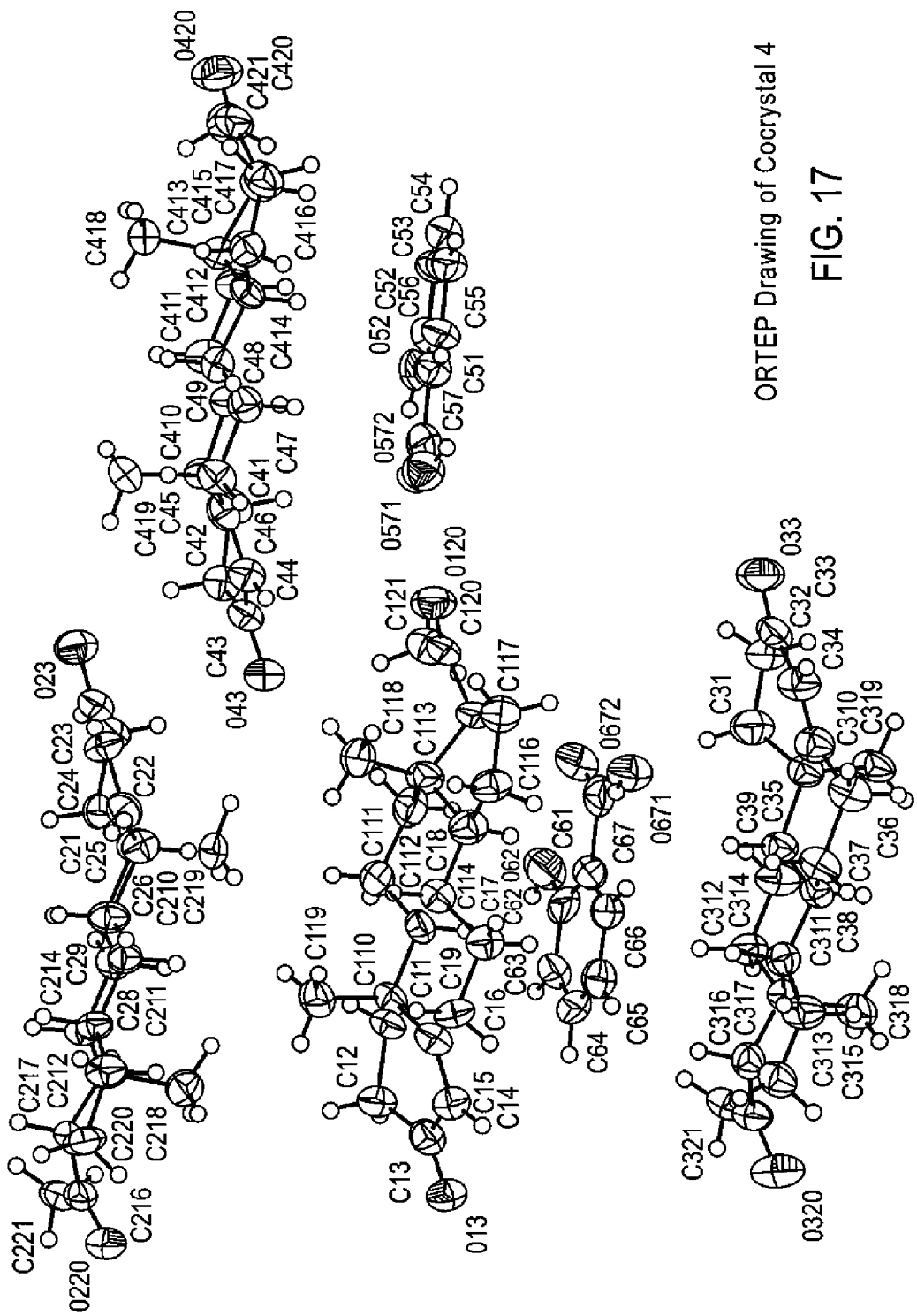
FIG. 17 is an ORTEP drawing of Cocrystal 4.

In a further embodiment of the invention, a cocrystal of progesterone:salicylic acid in a molar ratio of 2:1 (Cocrystal 4) is disclosed. The structure of Cocrystal 4 is set forth in FIG. 17.

Figure 18:
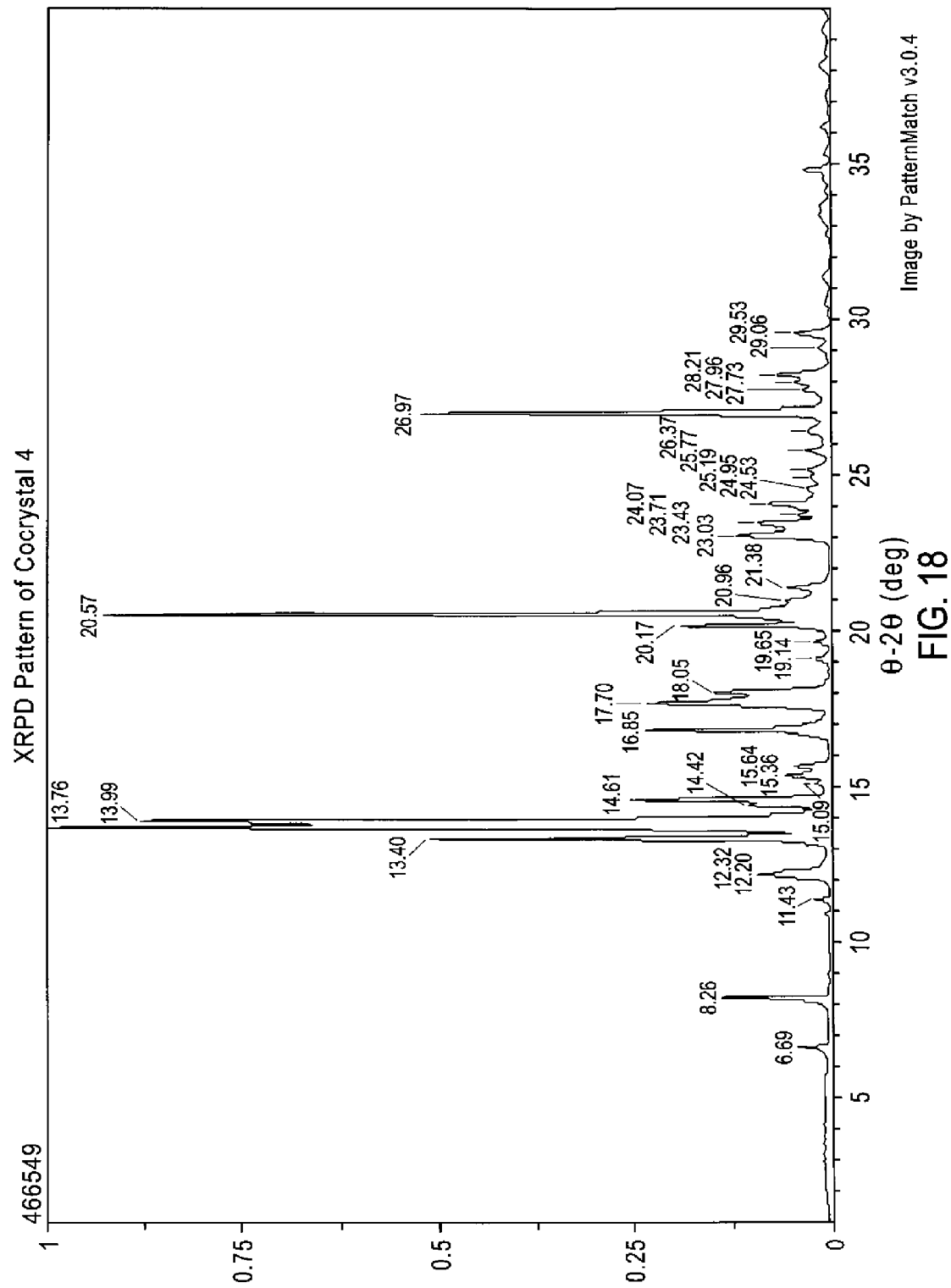
FIG. 18 is an XRPD pattern of Cocrystal 4.

The XRPD pattern corresponding to Cocrystal 4 is represented by FIG. 18. As can be readily determined, the XPRD pattern of FIG. 18 differs from those of FIGS. 2 and 13 and is not merely a linear superposition of the patterns as confirmed by the single crystal represented in FIG. 17, the parameters for which are set forth in Table 3.

TABLE 3

DATA AND DATA COLLECTION PARAMETERS FOR Cocrystal 4

| | |
|---|---|
| formula | $C_{49}H_{66}O_7$ |
| formula weight | 767.07 |
| space group | P1 (No. 1) |
| a, Å | 7.4530(2) |
| b, Å | 15.9667(5) |
| c, Å | 18.5079(4) |
| α, deg | 77.426(5) |
| β, deg | 81.393(6) |
| γ, deg | 77.875(6) |
| V, Å$^3$ | 2089.15(17) |
| Z | 2 |
| $d_{calc}$, g cm$^{-3}$ | 1.219 |
| crystal dimensions, mm | 0.20 × 0.10 × 0.05 |
| temperature, K | 150 |
| radiation (wavelength, Å) | Cu K$_\alpha$ (1.54184) |
| monochromator | Confocal optics |
| linear abs coef, mm$^{-1}$ | 0.630 |
| absorption correction applied | empirical |
| transmission factors: min, max | 0.87, 0.97 |
| diffractometer | Rigaku RAPID-II |
| h, k, l range | −8 to 8 −18 to 18 −21 to 22 |
| 2Θ range, deg | 4.92-133.17 |
| mosaicity, deg | 0.27 |
| programs used | SHELXTL |
| F$_{000}$ | 832.0 |
| weighting 1/[σ$^2$(Fo$^2$) + (0.1674P)$^2$ + 2.2275P] where P = (Fo$^2$ + 2Fc$^2$)/3 | |
| data collected | 42113 |
| unique data | 11439 |
| R$_{int}$ | 0.061 |
| data used in refinement | 11439 |
| cutoff used in R-factor calculations | F$_o^2$ > 2.0 σ (F$_o^2$) |
| data with I > 2.0 σ (I) | 6318 |
| refined extinction coef | 0.0012 |
| number of variables | 1026 |
| largest shift/esd in final cycle | 0.00 |
| R(F$_o$) [Σ |Fo − Fc|/Σ Fo] | 0.086 |
| R$_w$(F$_o^2$) [SQRT (Σ w (Fo$^2$ − Fc$^2$)$^2$/Σ w (Fo$^2$)$^2$)] | 0.198 |
| goodness of fit | 1.026 |
| absolute structure determination | Flack parameter (−0.1(3)) |
| | Hooft parameter (0.01(11)) |
| | Friedel Coverage 85% |

A pattern substantially the same as the pattern of FIG. 18 may be used to characterize Cocrystal 4. A smaller subset of the peaks identified in FIG. 18 may be used to characterize Cocrystal 4. For example, anyone or more of the peaks at about 8.3, 13.4, 13.8, 14.0, 14.6, 16.9, 17.7, 18.1, 20.2, 20.6, or 27.0 °2θ may be used to characterize Cocrystal 4.

Figure 19:
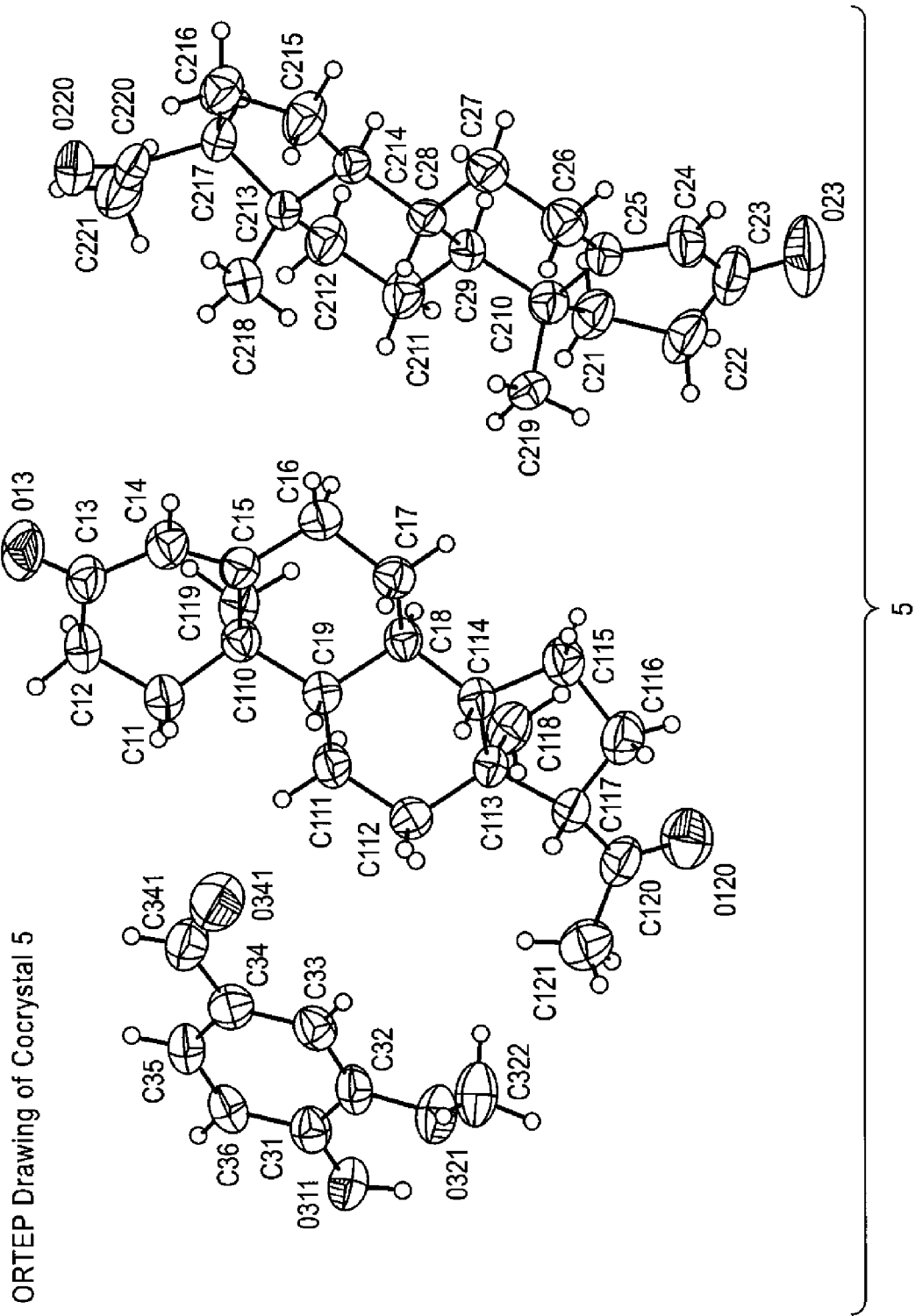
FIG. 19 is an ORTEP drawing of Cocrystal 5.

In a further embodiment of the invention, a cocrystal of progesterone:vanillin in a molar ratio of 2:1 (Cocrystal 5) is disclosed. The structure of Cocrystal 5 is set forth in FIG. 19.

Figure 35:
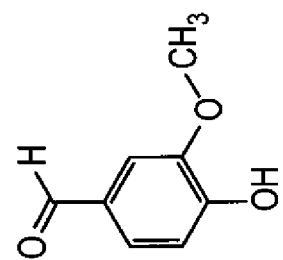
FIG. 35 shows the formula of Vanillin.

Vanillin has the formula shown in FIG. 35.

Figure 20:
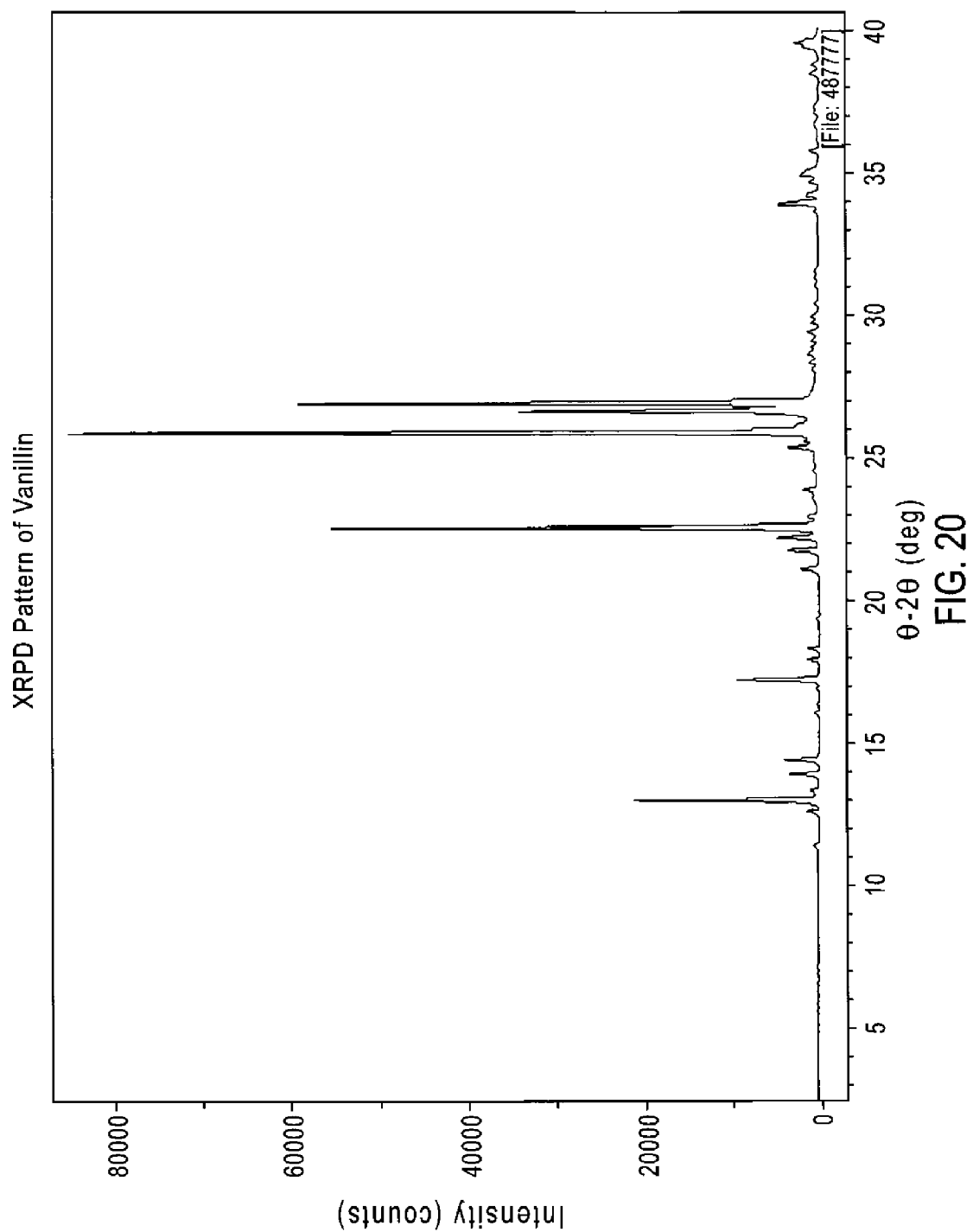
FIG. 20 is an XRPD pattern of vanillin.
Figure 21:
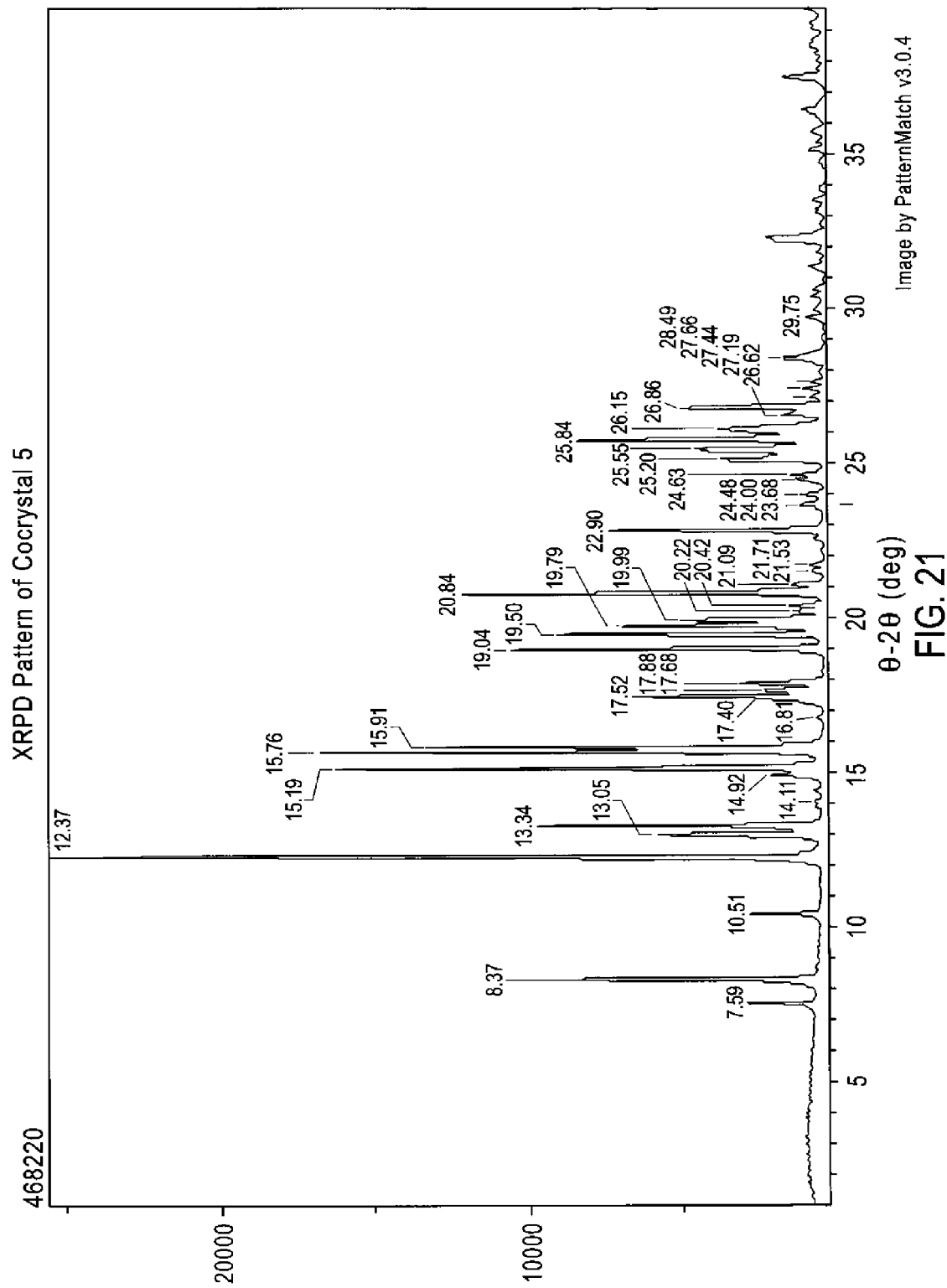
FIG. 21 is an XRPD pattern of Cocrystal 5.

The XRPD pattern of the vanillin used herein can be found at FIG. 20. The XRPD pattern corresponding to Cocrystal 5 is represented by FIG. 21. As can be readily determined, the XPRD pattern of FIG. 21 differs from those of FIGS. 2 and 10 and is not merely a linear superposition of the patterns as confirmed by the single crystal represented in FIG. 19, the parameters for which are set forth in Table 4.

TABLE 4

CRYSTAL DATA AND DATA COLLECTION PARAMETERS FOR Cocrystal 5

| | |
|---|---|
| formula | $C_{50}H_{68}O_7$ |
| formula weight | 781.10 |
| space group | $P2_1$ (No. 4) |
| a, Å | 7.4002(14) |
| b, Å | 21.0590(4) |
| c, Å | 14.3463(10) |
| β, deg | 104.262(11) |
| V, Å$^3$ | 2166.8(4) |
| Z | 2 |
| $d_{calc}$, g cm$^{-3}$ | 1.197 |
| crystal dimensions, mm | 0.20 × 0.20 × 0.10 |
| temperature, K | 150 |
| radiation (wavelength, Å) | Cu K$_\alpha$ (1.54184) |
| monochromator | confocal optics |
| linear abs coef, mm$^{-1}$ | 0.615 |
| absorption correction applied | empirical |
| transmission factors: min, max | 0.83, 0.94 |
| diffractometer | Rigaku RAPID-II |
| h, k, l range | −8 to 8 −25 to 24 −14 to 17 |
| 2Θ range, deg | 4.20-133.12 |
| mosaicity, deg | 0.13 |
| programs used | SHELXTL |
| F$_{000}$ | 848.0 |
| weighting 1/[σ$^2$(Fo$^2$) + (0.0393P)$^2$ + 0.3305P] where P = (Fo$^2$ + 2Fc$^2$)/3 | |
| data collected | 24498 |
| unique data | 7474 |
| R$_{int}$ | 0.024 |
| data used in refinement | 7474 |
| cutoff used in R-factor calculations | F$_o^2$ > 2.0 σ (F$_o^2$) |
| data with I > 2.0 σ (I) | 6272 |
| refined extinction coef | 0.0104 |
| number of variables | 526 |
| largest shift/esd in final cycle | 0.00 |
| R(F$_o$) [Σ |Fo − Fc|/Σ Fo] | 0.035 |
| R$_w$(F$_o^2$) [SQRT (Σ w (Fo$^2$ − Fc$^2$)$^2$/Σ w (Fo$^2$)$^2$)] | 0.081 |
| goodness of fit | 1.173 |
| absolute structure determination | Flack parameter (0.03(19)) Hooft parameter (0.04(4)) Friedel Coverage 96% |

A pattern substantially the same as the pattern of FIG. 21 may be used to characterize Cocrystal 5. A smaller subset of the peaks identified in FIG. 21 may be used to characterize Cocrystal 5. For example, anyone or more of the peaks at about 8.4, 10.5, 12.4, 13.1, 13.3, 15.2, 15.8, 15.9, 17.5, 19.0, 19.5, 19.8, 20.0, 20.8, 22.9, or 25.8 °2θ may be used to characterize Cocrystal 5.

Figure 28:
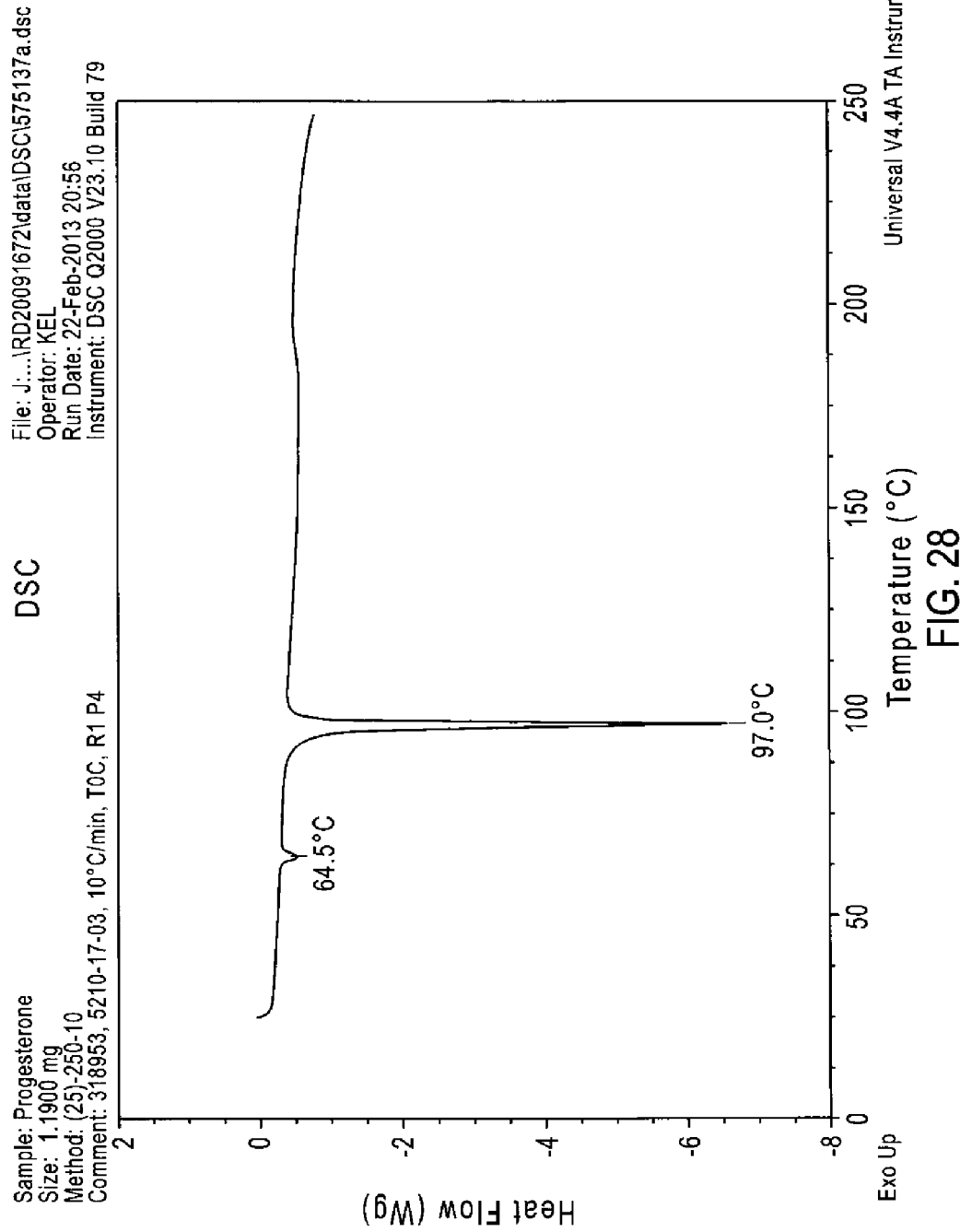
FIG. 28 is a DSC thermogram of Cocrystal 5.

Cocrystal 5 may be characterized by its thermal characteristics. For example, FIG. 28 is a DSC thermogram of Cocrystal 5 and it exhibits an endotherm maximum at about 97° C. under the conditions set forth herein for DSC in FIG. 11. Cocrystal 5 may be characterized by DSC alone or in combination with XRPD diffraction pattern or one or more of the peaks set forth herein.

Figure 29:
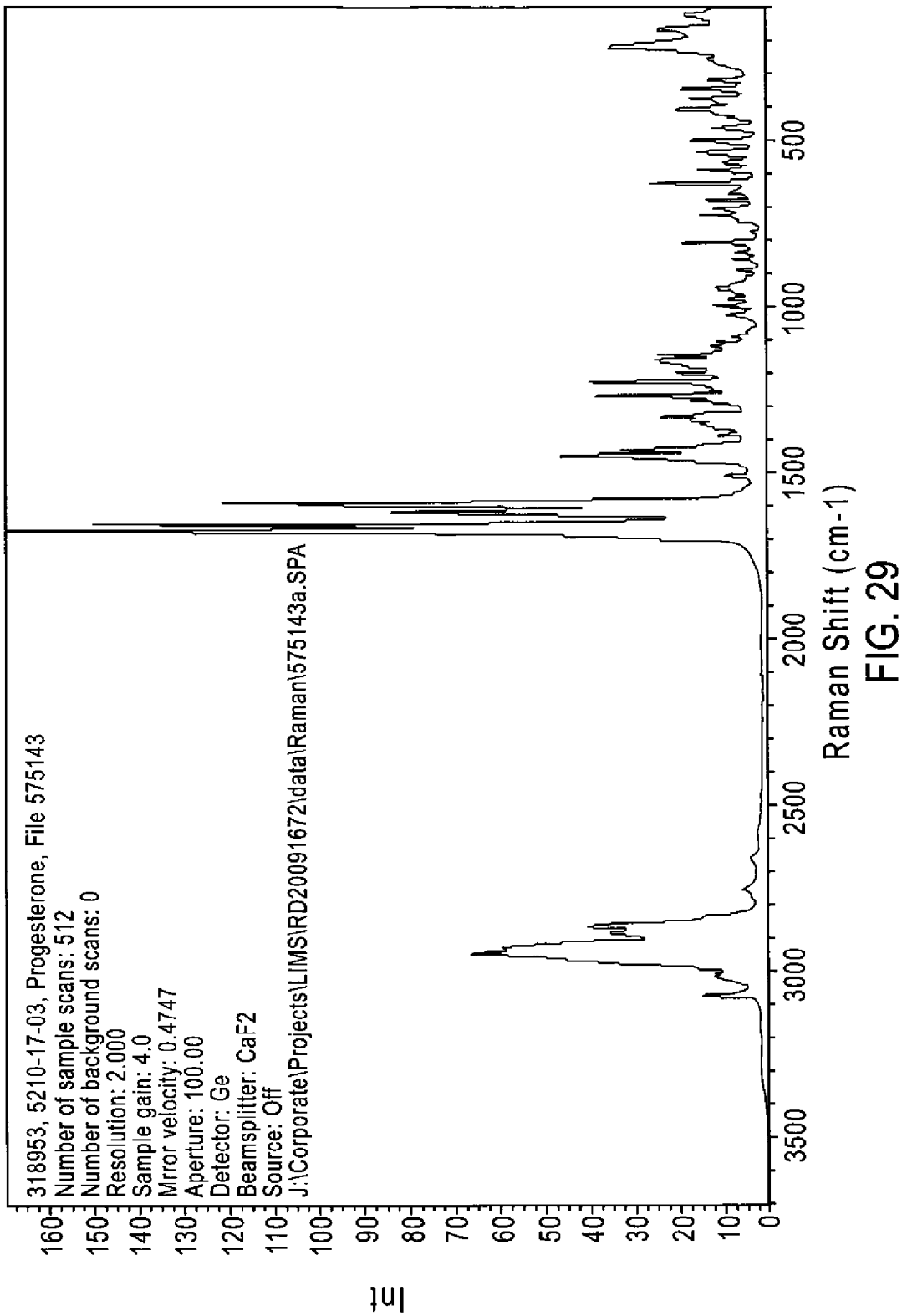
FIG. 29 is a Raman spectrum of Cocrystal 5.

Cocrystal 5 may be characterized by the Raman spectrum in FIG. 29. When considering just Raman spectroscopy, the entire Rama spectrum may be used to characterized Cocrystal 5 or a subset thereof. For example, anyone of the peaks at about 1675, 1657, or 1594 cm$^{-1}$, or others may be used alone or in combination to characterize Cocrystal 5.

Figure 30:
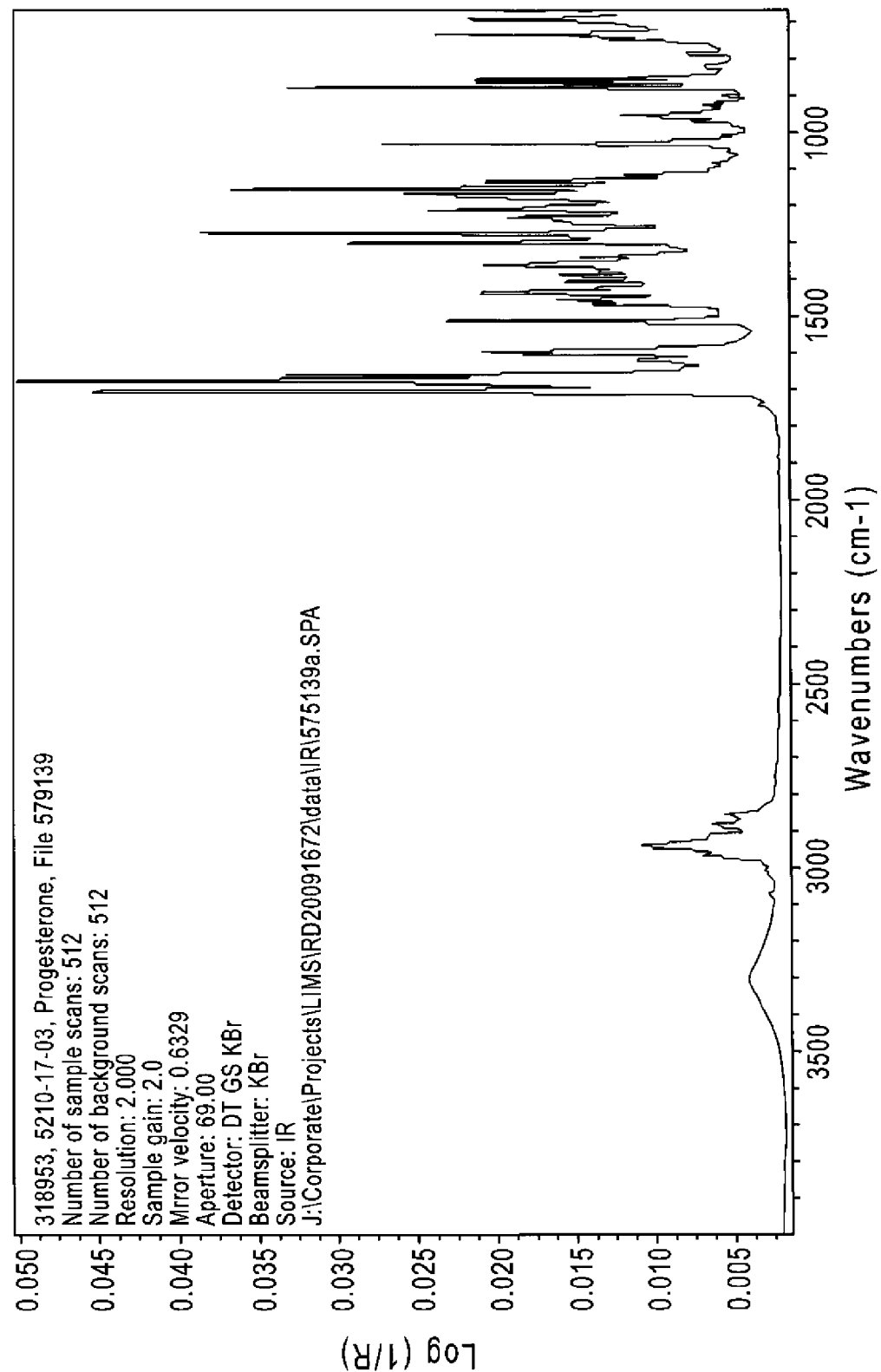
FIG. 30 is an FT-infrared spectrum of Cocrystal 5.

Cocrystal 5 may be characterized by the FT-Infrared spectrum in FIG. 30. When considering just FT-Infrared spectroscopy, the entire FT-IR spectrum may be used to characterize Cocrystal 5, or a subset thereof. For example, anyone of the peaks at about 1673, 1700, or 1656 or others may be used alone or in combination to characterize Cocrystal 5.

Cocrystal 5 may be characterized by one or more of the Raman, FT-IR, DSC, and x-ray techniques as set forth herein. For example, Cocrystal 5 may be characterized by a peak at about 12.4°2θ, a DSC endotherm maximum at about 97° C. In another embodiment, a Raman peak at about 1675 cm$^{-1}$ and FT-IR peak at about 1700 cm$^{-1}$ may be used to characterize Cocrystal 5.

Figure 27:
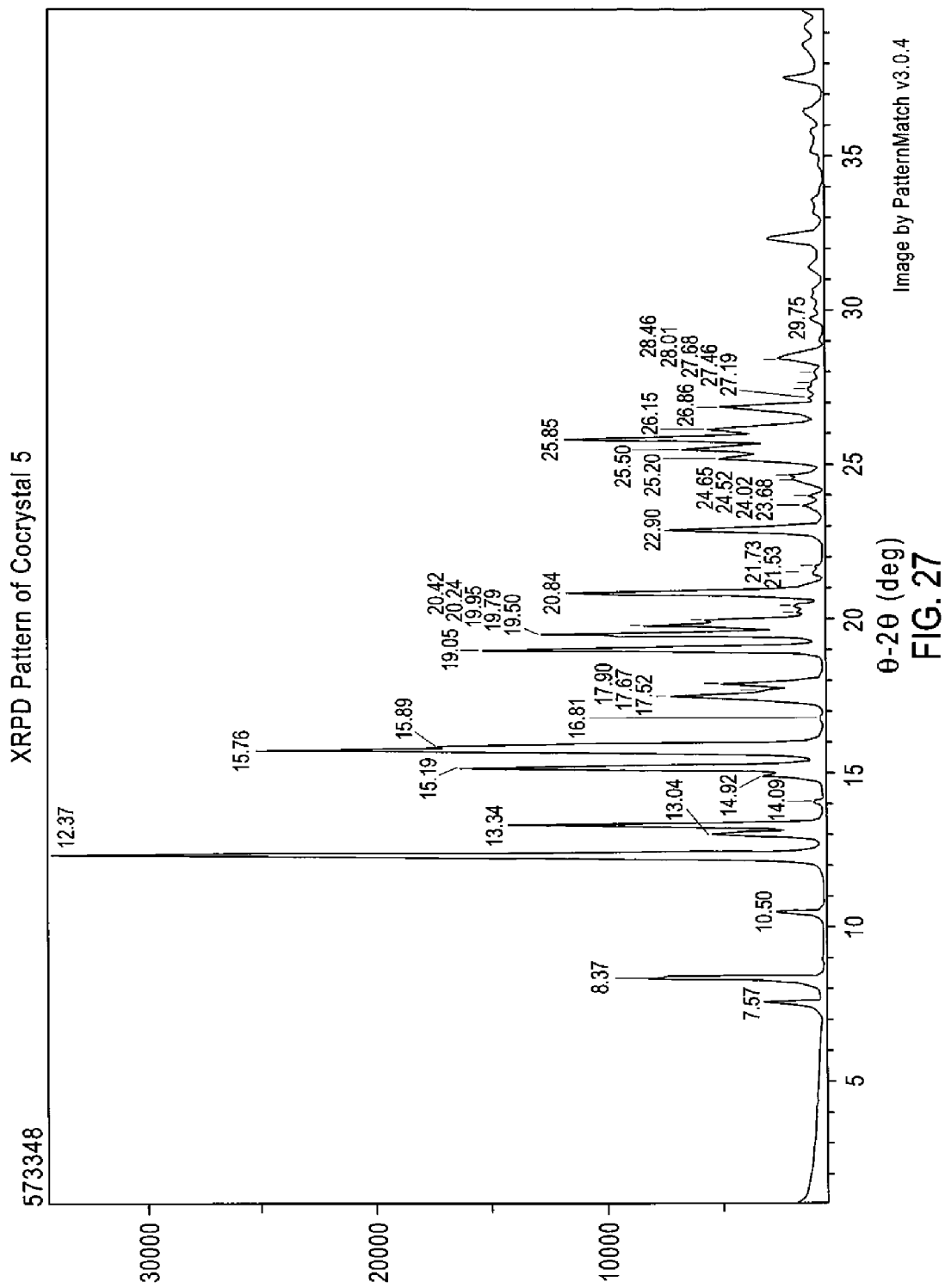
FIG. 27 is an XRPD pattern of Cocrystal 5.

FIG. 27 represents an additional XRPD pattern of Cocrystal 5. FIG. 21 was found to contain a small amount of vanillin starting material. The Cocrystal 5 prepared in Example 5B, yielded the pattern of FIG. 27 which contained no detectable vanillin. The data represented in FIGS. 28, 29, and 30 were collected on this sample.

Figure 36:
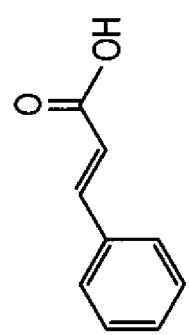
FIG. 36 shows the structure of cinnamic acid.

In yet another embodiment of the invention, a cocrystal of progesterone:cinnamic acid (Cocrystal 6) is disclosed. The structure of cinnamic acid is shown in FIG. 36.

Figure 22:
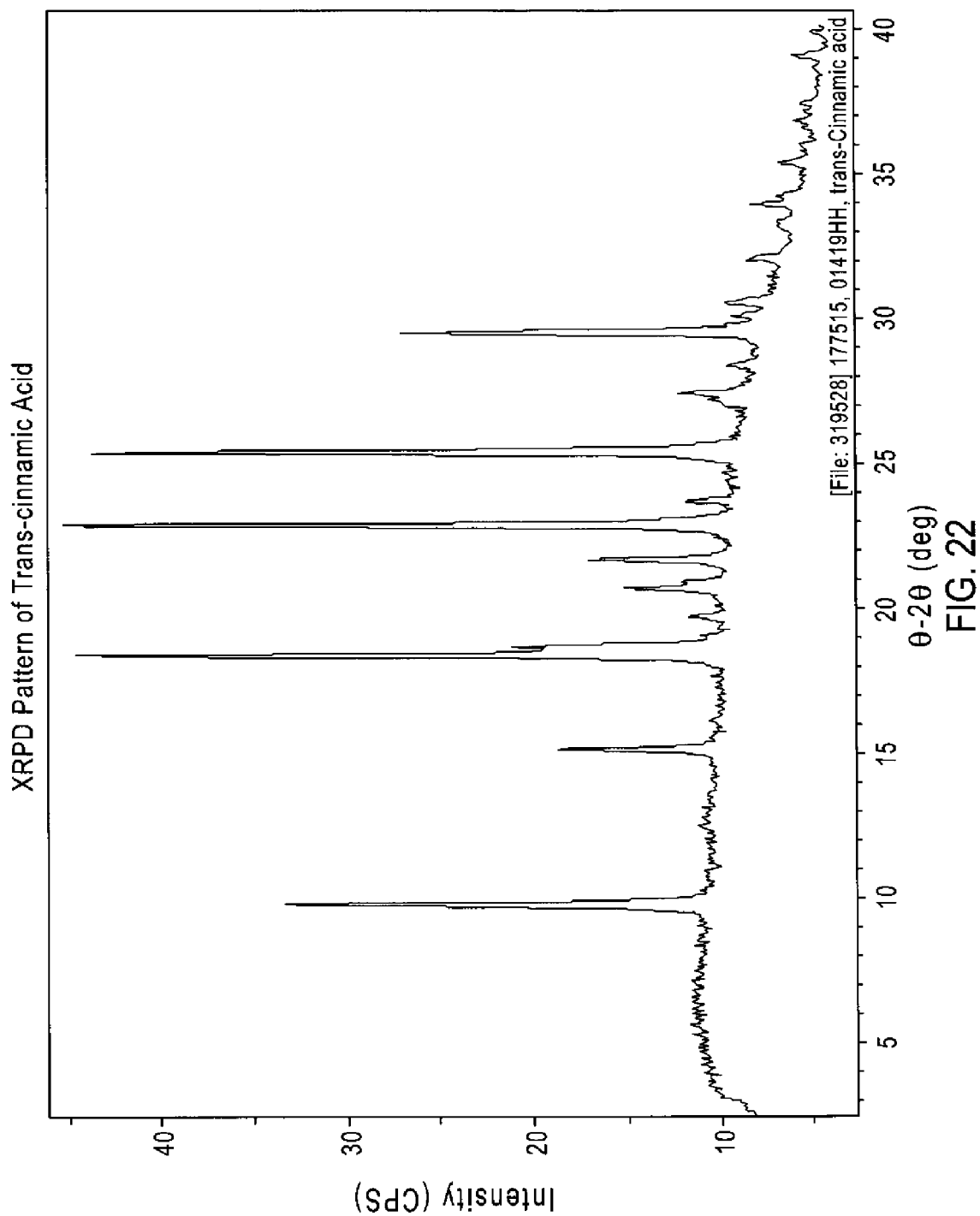
FIG. 22 is a XRPD pattern of cinnamic acid.
Figure 23:
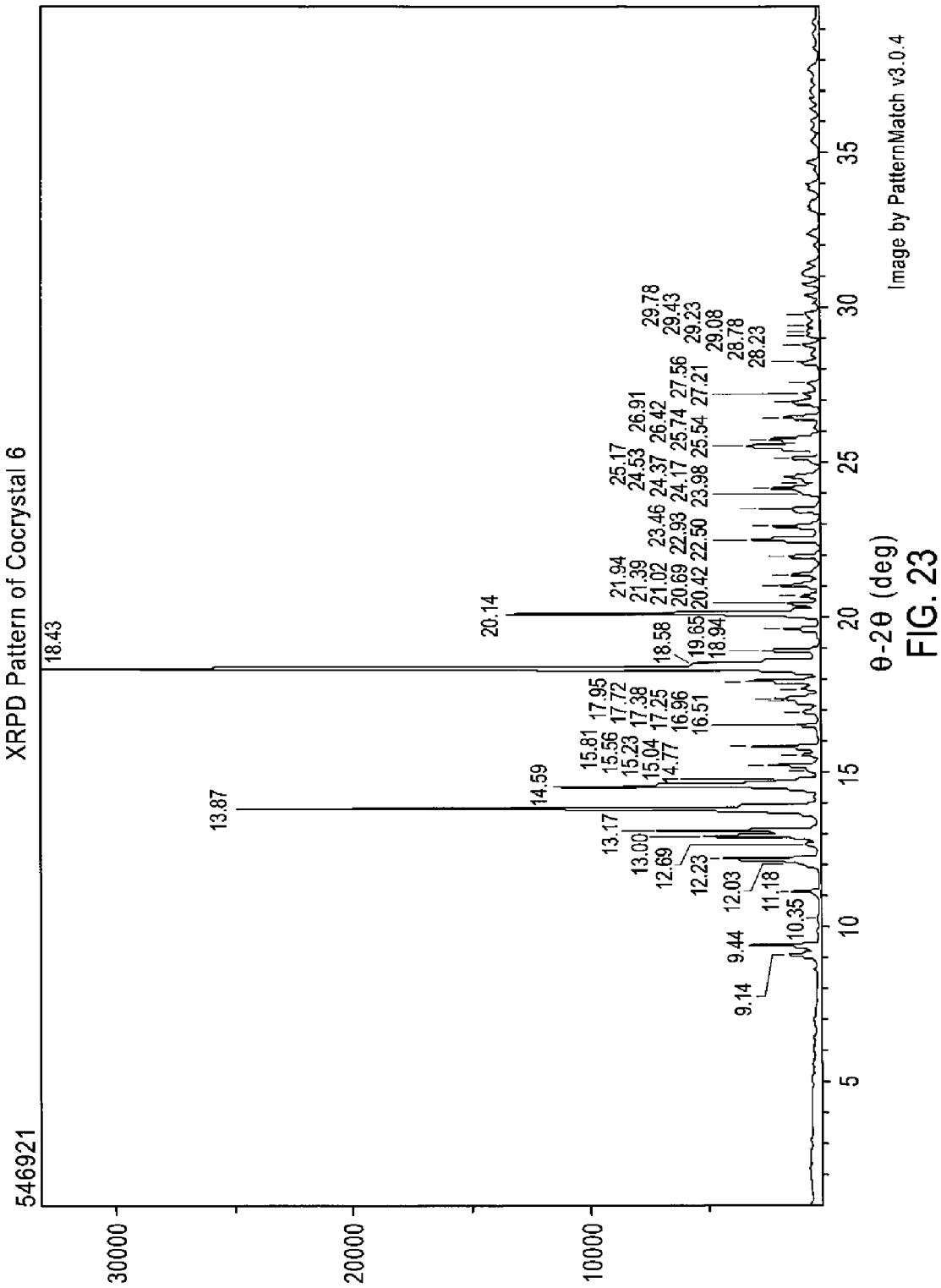
FIG. 23 is an XRPD pattern of Cocrystal 6.

The XRPD pattern of the cinnamic acid starting material used herein can be found in FIG. 22. The XRPD pattern corresponding to Cocrystal 6 is represented by FIG. 23. As can be readily determined, the XPRD pattern of FIG. 23 differs from those of FIGS. 2 and 22 and is not merely a linear superposition of the patterns.

A pattern substantially the same as the pattern of FIG. 23 may be used to characterize Cocrystal 6. A smaller subset of the peaks identified in FIG. 23 may be used to characterize Cocrystal 6. For example, anyone or more of the peaks at about 9.4, 12.2, 13.0, 13.2, 13.9, 14.6, 18.4, or 20.1°2θ may be used to characterize Cocrystal 6.

Figure 24:
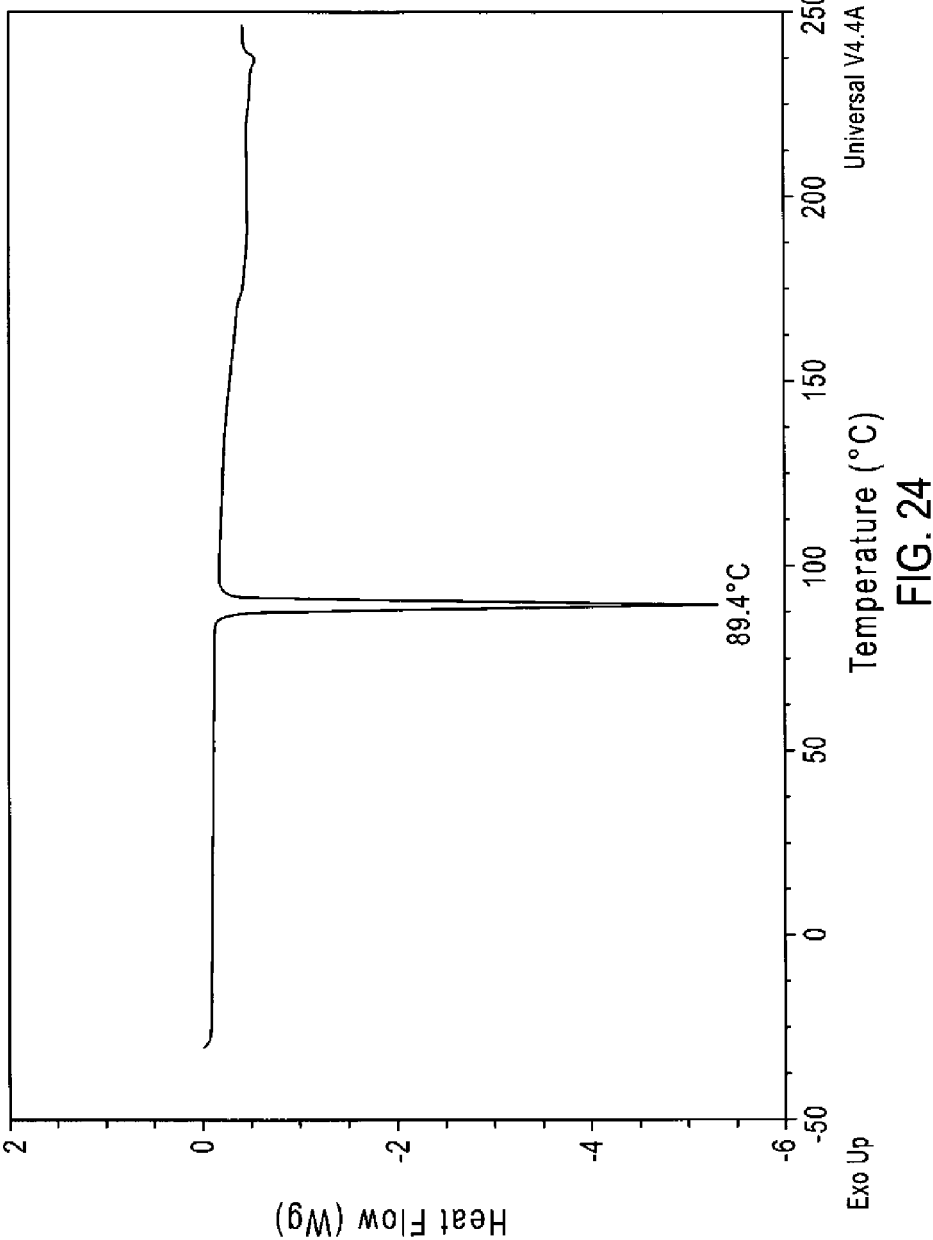
FIG. 24 is a DSC thermogram of Cocrystal 6.

Cocrystal 6 may be characterized by its thenal characteristics. For example, FIG. 24 is a DSC thermogram of Cocrystal 6 and it exhibits an endotherm at about 89° C. under the conditions set forth herein for DSC in FIG. 24. Cocrystal 6 may be characterized by DSC alone or in combination with XRPD diffraction pattern or one or more of the peaks set forth herein.

Figure 25:
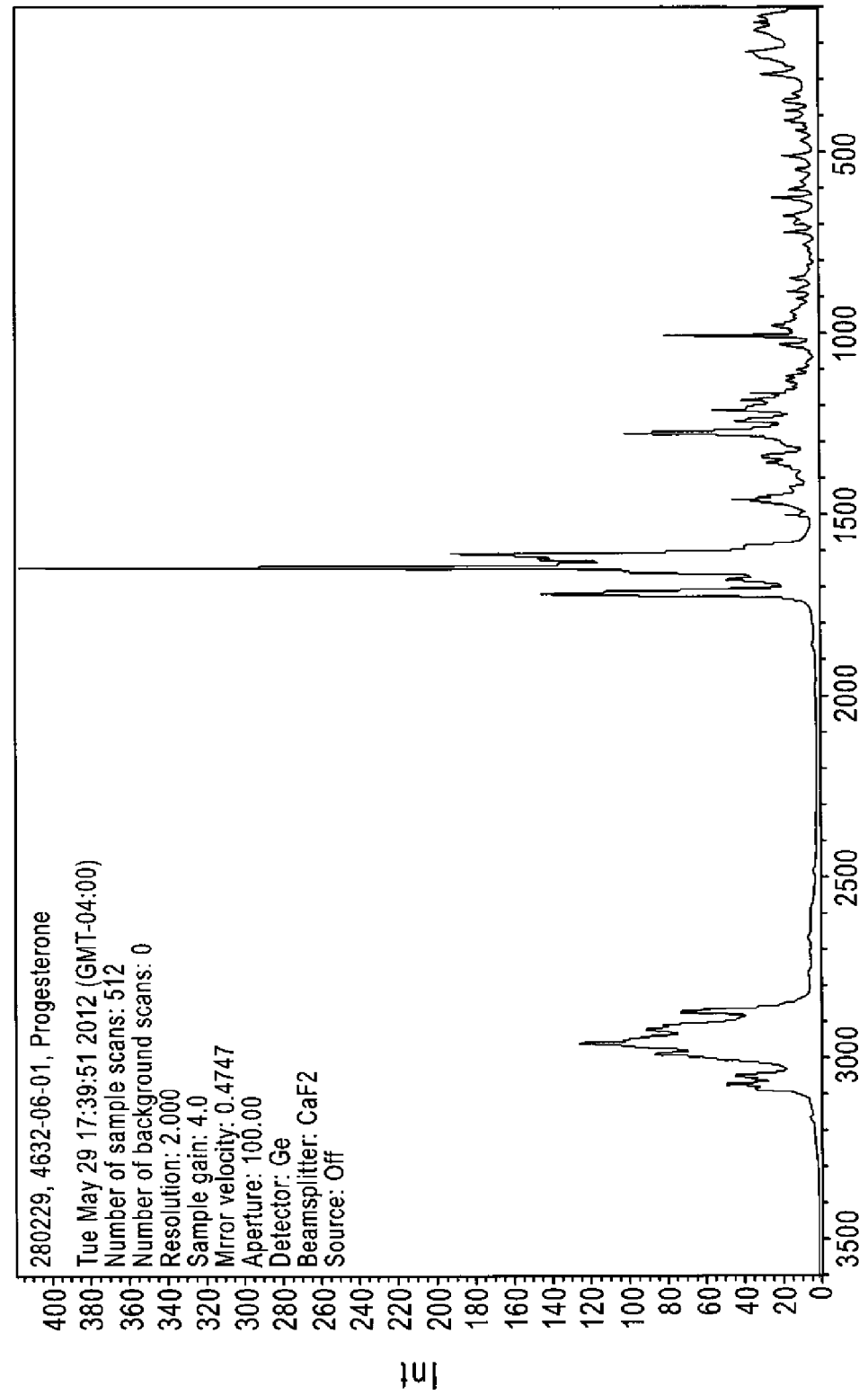
FIG. 25 is a Raman spectrum of Cocrystal 6.

Cocrystal 6 may be characterized by the Raman spectrum in FIG. 25. When considering just Raman spectroscopy, the entire Raman spectrum may be used to characterized Cocrystal 6 or a subset thereof. For example, anyone of the peaks at 1268, 1599, 1614, 1633, or 2940 cm$^{-1}$ or others may be used alone or in combination to characterize Cocrystal 6.

Cocrystal 6 may be characterized by one or more of the infrared, DSC, and x-ray techniques as set forth herein. For example, Cocrystal 6 may be characterized by a peak at about 13.9 °2θ, a DSC onset temperature of about 89° C. Further, an infrared peak at about 1268 cm$^{-1}$ may be used to characterize Cocrystal 6.

Figure 37:
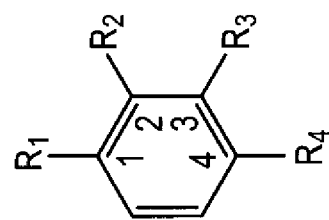
FIG. 37 shows the structure of a cocrystal of progesterone with a coformer of structure of Formula I, according to an exemplary embodiment.

In yet another embodiment, the invention is directed to a cocrystal of progesterone with a co former of the structure of Formula I, an exemplary embodiment of which is shown in FIG. 37, wherein R1 is H, OH, C(O)H, alkyl-CO$_2$H, or alkenyl-CO$_2$H; R$_2$ is H or OH; R$_3$ is H, OH, or O-alkyl; and R$_4$ is H or OH provided that at least one of R$_1$, R$_2$, R$_3$, and R$_4$ is not H or OH and that at least one of R$_1$, R$_2$, R$_3$, and R$_4$ contain a carbonyl moiety. Included within alkyl and alkenyl are carbon chains of 1, 2, 3, 4, or 5 atoms.

In another embodiment, R$_1$ is C(O)H, CO$_2$H or alkenyl-CO$_2$H; R$_2$ is H or OH; R$_3$ is H or O-alkyl; and R$_4$ is H or OH.

EXAMPLES

All chemicals were obtained from commercial sources and used without further purification. Progesterone and its cocrystals were treated as light sensitive materials.

XRPD patterns were collected with a PANalytical X'Pert PRO MPD diffractometer using an incident beam of Cu radiation produced using an Optix long, fine-focus source. An elliptically graded multilayer mirror was used to focus Cu Kα X-rays through the specimen and onto the detector. Prior to the analysis, a silicon specimen (NIST SRM 640d) was analyzed to verify the observed position of the Si 111 peak is consistent with the NIST-certified position. A specimen of the sample was sandwiched between 3-μm-thick films and analyzed in transmission geometry. A beam-stop, short antiscatter extension, antiscatter knife edge, were used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v.2.2b.

Solution 1H NMR spectra were acquired at ambient temperature with a Varian UNITYINOVA-400 spectrometer. Samples were dissolved in DMSO-d6 containing TMS. The spectra was referenced to internal tetramethylsilane (TMS) at 0.0 ppm.

DSC analyses were performed using a TA Instruments 2920 and Q2000 differential scanning calorimeter. Temperature calibration was performed using NIST-trace-able indium metal. Samples were placed into an aluminum DSC pan, covered with a lid (T0C-Tzero crimped), and the weight was accurately recorded. A weighed aluminum pan configured as the sample pan was placed on the reference side of the cell. The data acquisition parameters and pan configuration for each thermogram are displayed on images. The method code on the thermogram for each corresponding Figure is an abbreviation for the start and end temperature as well as the heating rate; e.g., –30-250-10 means "from –30° C. to 250° C., at 10° C./min."

Raman spectra were acquired on a FT-Raman 960 spectrometer (Thermo Nicolet) equipped with a germanium (Ge) detector. Wavelength verification was performed using sulfur and cyclohexane. Each sample was prepared for analysis by placing the sample into a pellet holder, Approximately 0.505 W of Nd:YV04 laser power (1064 nm excitation wavelength) was used to irradiate the sample. The data acquisition parameters for each pattern are displayed in each corresponding Figure.

Example 1—Cocrystal 1

1:1 Progesterone:Vanillic Acid Cocrystal

Crystals for Single Crystal Structure Determination

A mixture of progesterone (250.3 mg, ~0.8 mmol) and vanillic acid (133.5 mg, ~0.8 mmol) was suspended in 1 mL of a 37.5% solution of ethyl acetate in heptane. The suspension was then transferred to a well of a metal block equipped with a hotplate and a stirrer and preheated to ~60° C. Additional 5 mL of the 37.5% ethyl acetate solution in heptane and 3.9 mL of pure ethyl acetate were gradually added to the suspension with stirring to obtain clear solution (~25 mg/mL of progesterone in a final 62/38% ethyl acetate/heptane). The solution was then cooled slowly to ambient temperature by switching the heat/stirring source off and remaining on the metal block. The resulting crystals were isolated by vacuum filtration after approximately one day and dried on a vacuum filter for ~2-5 min. Suitable crystals were selected for single crystal structure determination.

Preparation for Physical Characterization

A mixture of progesterone (1296.0 mg, ~4.1 mmol) and vanillic acid (692.9 mg, ~4.1 mmol) was suspended in 18 mL of a methyl tert-butyl ether/heptane solvent mixture (33/66%). Seeds of 1:1 progesterone:vanillic acid cocrystal were added to the suspension. The suspension was stirred at ambient temperature for approximately two days. The resulting solids were isolated by vacuum filtration, washed with 2 mL of chilled methyl tert-butyl ether and dried on vacuum filter for 2-3 min. Recovered solids (1858.2 mg) were vacuum dried at ambient temperature for approximately three days and analyzed by XRPD. The pattern was consistent with an XRPD pattern of an 1:1 progesterone:vanillic acid cocrystal.

Example 2—Cocrystal 2

2:1 Progesterone:Benzoic Acid Hemi-Hydrate Cocrystal

Preparation of Seeds

A mixture of progesterone (106.4 mg, ~0.3 mmol) and benzoic acid (42.3 mg, ~0.3 mmol) was dissolved in 4 mL of nitromethane. The solution was then concentrated by partial evaporation of solvent at ambient from a container covered with aluminum foil with pin holes. Solids resulted were isolated by decantation and dried under a nitrogen stream for approximately two minutes. The dried solids were analyzed by XRPD and were consistent with a 2:1 progesterone:benzoic acid hemi-hydrate cocrystal containing small amount of benzoic acid.

Crystals for Single Crystal Structure Determination

A mixture of progesterone (286.0 mg, ~0.9 mmol) and benzoic acid (111.9 mg, ~0.9 mmol) was dissolved in 0.5 mL of acetonitrile at ~60° C. using a hot plate. The solution was removed from a heat source and cooled to ambient temperature. Seeds of a 2:1 progesterone:benzoic acid hemi-hydrate cocrystal prepared as described were added to the clear solution. The precipitate resulted was partially re-dissolved in approximately 1 mL of ethyl acetate. The solution was then concentrated by partial evaporation of solvent at ambient from an open container. Final solids with needle-like morphology were isolated by vacuum filtration and air dried. Suitable crystals were selected for single crystal structure determination. Bulk material was analyzed by XRPD and was consistent with a 2:1 progesterone:benzoic acid hemi-hydrate cocrystal containing small amount of benzoic acid.

Preparation for Physical Characterization

A mixture of progesterone (314.0 mg, ~1 mmol) and benzoic acid (121.8 mg, ~1 mmol) was dissolved in 0.4 mL of ethyl acetate at ~60° C. using a hot plate. The solution was cooled to ambient temperature. Seeds of a 2:1 progesterone:benzoic acid hemi-hydrate cocrystal prepared as described were added to the clear solution. The precipitate resulted was diluted with additional, 0.4 mL of ethyl acetate and isolated by vacuum filtration. The final solids were washed with ethyl acetate (2 mL), and air dried.

A mixture of progesterone (356.7 mg, ~1.1 mmol) and benzoic acid (138.1 mg, ~1.1 mmol) was dissolved in 1 mL of nitromethane at ambient temperature. Seeds of a 2:1 progesterone:benzoic acid hemi-hydrate cocrystal prepared as described were added to the clear solution. The solution was then concentrated by partial evaporation of solvent from a container covered with aluminum foil with pin holes. Final solids were isolated by vacuum filtration and air dried.

Progesterone (248.0 mg, ~0.8 mmol) was dissolved in 1 mL of acetonitrile at ~50° C. using a hot plate. Solids of benzoic acid were gradually added to the stirring solution. The clear solution was then cooled to ambient temperature by switching the heat source off and remaining on the hot plate. The clear ambient solution was then stored at subambient temperature (–25° C. to –10° C.) for approximately one day. The solids resulted were isolated cold by vacuum filtration, dried on vacuum filter for about 5 minutes.

Progesterone (172.1 mg, ~0.5 mmol) was dissolved in 2 mL of acetonitrile at ambient temperature. Solids of benzoic acid were gradually added to the stirring solution as to have solids remaining. After approximately one day of stirring at ambient temperature, the remaining solids were filtered off. The filtrate was evaporated to dryness at ambient temperature.

All solids isolated were analyzed by XRPD and were consistent with a 2:1 progesterone:benzoic acid hemihydrate cocrystal containing various amounts of benzoic acid. The samples were then combined and suspended in 1.4 mL of methyl tert-butyl ether. The suspension was stirred at ambient temperature for approximately two hours. The final solids were isolated by vacuum filtration, washed with chilled methyl tert-butyl ether, dried on vacuum filter for ~5 minutes and analyzed by XRPD. The pattern was consistent with a 2:1 progesterone:benzoic acid hemi-hydrate cocrystal.

Example 3—Cocrystal 3

1:1 Progesterone:Salicylic Acid Cocrystal

Preparation of Seeds

A mixture of progesterone (111.5 mg, ~0.4 mmol) and salicylic acid (51.5 mg, ~0.4 mmol) was dissolved in 3.9 mL of methanol/nitromethane/(20/80). The solution was then evaporated at ambient from a container covered with aluminum foil with pin holes. Solids and oil were produced. The oil was discarded. The solids separated from oil were analyzed by XRPD and were consistent with a 1:1 progesterone:salicyic acid cocrystal.

Preparation for Physical Characterization

A mixture of progesterone (1045.4 mg, ~3.3 mmol) and salicylic acid (459.2 mg, ~3.3 mmol) was dissolved in 1 mL of a methanol/nitromethane solvent mixture (20/80%). The solution was then concentrated by partial evaporation of solvent from an open container and under a nitrogen stream and repeatedly seeded with a 1:1 progesterone:salicylic acid cocrystal prepared as described above. The evaporation was discontinued when dissolution of seeds was not achieved and solids precipitated. The solids were isolated by vacuum filtration, dried on vacuum filter for approximately 30 minutes and analyzed by XRPD (832.5 mg, ~56% yield).

Example 4—Cocrystal 4

2:1 Progesterone:Salicylic Acid Cocrystal

Preparation of Seeds

A mixture of progesterone (285.5 mg, ~0.9 mmol) and salicylic acid (125.6 mg, ~0.9 mmol) was dissolved in 1.2 mL of ethyl acetate at −70° C. using a hotplate. The solution was then cooled slowly to ambient temperature by switching the heat source off. Seeds of 1:1 progesterone:salicylic acid cocrystal were added to the clear solution followed by gradual addition of 2 mL of heptane. The solution was left at ambient undisturbed for approximately two days. Solids resulted were isolated by vacuum filtration, dried on vacuum filter for ~2 minutes and analyzed by XRPD. The solids were consistent with a 2:1 progesterone:salicylic acid cocrystal containing small amount of salicylic acid.

Crystals for Single Crystal Structure Determination

A mixture of progesterone (109.8 mg, ~0.3 mmol) and salicylic acid (47.5 mg, ~0.3 mmol) was suspended in 0.5 mL of ethyl acetate/heptane (20/80). The suspension was then transferred to a hotplate preheated to ~70° C. and equipped with a stirrer. Additional 0.5 mL of the 20/80% ethyl acetate/heptane solvent mixture were added to the suspension with stirring to obtain clear solution (~110 mg/mL of progesterone). The solution was then cooled slowly to −50° C. (10° C./min cooling rate). Seeds of a 2:1 progesterone:salicylic acid cocrystal prepared as described above were added at ~50° C. and remained undissolved. Cooling was continued to ambient temperature resulting in rod-like crystals. Suitable crystals were selected for single crystal structure determination.

Example 5A—Cocrystal 5

2:1 Progesterone:Vanillin Cocrystal

Preparation of Seeds

A mixture of progesterone (288.3 mg, ~0.9 mmol) and vanillin (140.0 mg, ~0.9 mmol) was suspended at ambient temperature in 1 mL of a 37.5% solution of ethyl acetate in heptane. The suspension was then transferred to a well of a metal block equipped with a hotplate and a stirrer and preheated to ~60° C. The solution resulted was stirred at ~60° C. for approximately forty minutes. The slightly cloudy solution was then cooled slowly to ambient temperature by switching the heat/stirring source off and remaining on the metal block. Two liquid phases produced were left undisturbed at ambient temperature for ~2 days. The solids were isolated by vacuum filtration, dried on vacuum filter for 2-5 minutes and analyzed by XRPD. The solids were consistent with a 2:1 progesterone:vanillin cocrystal containing small amount of vanillin.

Example 5B—Cocrystal 5

A mixture of progesterone (201.6 mg, ~1 mmol) and vanillin (78.4 mg (~0.8 mmol)) was suspended in 1 mL of di-isopropyl ether. The suspension was then stirred at ambient temperature using a magnetic stirrer for approximately seven days. Additional 0.5 mL of di-isopropyl ether was added after ~3 days of stirring. Solids were isolated by vacuum filtration. The solids were analyzed by XRPD (FIG. 27) and were consistent with a 2:1 progesterone:vanillin cocrystal.

Crystals for Single Crystal Structure Determination

A mixture of progesterone (106.4 mg, ~0.3 mmol) and vanillin (49.2 mg, ~0.3 mmol) was suspended in 0.5 mL of ethyl acetate/heptane (20/80). The suspension was then transferred to a hotplate preheated to ~70° C. and equipped with a stirrer. Additional 2 mL of the 20/80 ethyl acetate/heptane solvent mixture were added to the suspension with stirring to obtain clear solution (~43 mg/mL of progesterone). The solution was then cooled slowly to ~50° C. (10° C./min cooling rate). Seeds of a 2:1 progesterone:vanillin cocrystal prepared as described above were added at ~50° C. and remained undissolved. Cooling was continued to ambient temperature. Suitable crystals were selected for single crystal structure determination.

Example 6—Cocrystal 6

Progesterone: Trans-Cinnamic Acid Cocrystal

Preparation of Seeds

A mixture of progesterone (96.7 mg, ~0.3 mmol) and trans-cinnamic acid (45.2 mg, ~0.3 mmol) was suspended at ambient temperature in 0.25 mL of methyl tertbutyl ether. The suspension was then stirred at ambient temperature for approximately three days. Solids were isolated by decantation, air dried at ambient temperature for ~2 days and analyzed by XRPD. The solids were consistent with a progesterone:cinnamic acid cocrystal containing small amount of unidentified material.

Preparation for Physical Characterization

A mixture of progesterone (750.0 mg, ~2.4 mmol) and trans-cinnamic acid (354.4 mg, ~2.5 mmol) was dissolved in 36 mL of a diisopropyl ether/heptane solvent mixture (50/50%) at ~60° C. The clear solution was then cooled slowly to ~45° C. Seeds of progesterone:cinnamic acid cocrystal were added, and the resulting suspension was stirred at ~45° C. for approximately 20 minutes. The suspension was cooled to ambient temperature by switching the heat/stirring source off. Solids were recovered by vacuum filtration (598.1 mg).

This invention also relates to pharmaceutical compositions containing cocrystals of the present invention. These compositions can be utilized to achieve the desired pharmacological effect by administration to a patient in need thereof including, but not limited to, progesterone supplementation or replacement treatment for infertile women with progesterone deficiency or secondary amenorrhea. A patient, for the purpose of this invention, is a mammal, including a human, in need of treatment for the particular condition or disease including, but not limited to, progesterone supplementation or replacement treatment for infertile women with progesterone deficiency or secondary amenorrhea. Therefore, the present invention includes pharmaceutical compositions which are comprised of at least one pharmaceutically acceptable carrier and a cocrystal of the present invention. A pharmaceutically acceptable carrier is any carrier which is relatively non-toxic and innocuous to a patient at concentrations consistent with effective activity of the active ingredient so that any side effects ascribable to the carrier do not vitiate the beneficial effects of the active ingredient. A pharmaceutically effective amount of compound is that amount which produces a result or exerts an influence on the particular condition being treated. The compound of the cocrystals of the present invention can be administered with pharmaceutically-acceptable carriers well known in the art using any effective conventional dosage unit forms, including immediate, slow and timed release preparations, orally, parenterally, topically, nasally, ophthalmically, optically, sublingually, rectally, vaginally, and the like.

What is claimed is:

1. A cocrystal of progesterone and a coformer selected from the group consisting of vanillic acid, benzoic acid, salicylic acid, cinnamic acid, and vanillin.

2. The cocrystal of claim 1 wherein the coformer is vanillic acid.

3. The cocrystal of claim 2, wherein the molar ratio of progesterone to vanillic acid in the cocrystal is 1:1.

4. The cocrystal of claim 1, wherein the coformer is benzoic acid.

5. The cocrystal of claim 4, wherein the molar ratio of progesterone to benzoic acid is 2:1.

6. The cocrystal of claim 5, wherein the cocrystal is a hemihydrate.

7. The cocrystal of claim 1, wherein the coformer is salicylic acid.

8. The cocrystal of claim 7, wherein the molar ratio of progesterone to salicylic acid is 1:1.

9. The cocrystal of claim 7, wherein the molar ratio of progesterone to salicylic acid is 2:1.

10. The cocrystal of claim 1, wherein the coformer is vanillin.

11. The cocrystal of claim 10, wherein the molar ratio of progesterone to vanillin is 2:1.

12. The cocrystal of claim 1, wherein the coformer is cinnamic acid.

13. The cocrystal of claim 12, wherein the coformer is trans-cinnamic acid.

14. A pharmaceutical composition comprising a cocrystal of claim 1 and at least one pharmaceutically acceptable carrier.

15. The pharmaceutical composition of claim 14, wherein the coformer is vanillic acid.

16. The pharmaceutical composition of claim 14, wherein the coformer is benzoic acid.

17. The pharmaceutical composition of claim 14, wherein the coformer is salicylic acid.

18. The pharmaceutical composition of claim 14, wherein the coformer is vanillin.

19. The pharmaceutical composition of claim 14, wherein the coformer is cinnamic acid.

20. A method of supplementing progesterone in women, said method comprising:
    administering to a female subject in need thereof a pharmaceutical composition of claim 14.

* * * * *